US010948746B2

(12) United States Patent
Langenwalter et al.

(10) Patent No.: US 10,948,746 B2
(45) Date of Patent: Mar. 16, 2021

(54) GOGGLE WITH REPLACEABLE LENS

(71) Applicant: Smith Sport Optics, Inc., Portland, OR (US)

(72) Inventors: Keith Langenwalter, Portland, OR (US); Eric Thorsell, Portland, OR (US); John Ohran, West Linn, OR (US); Will McNeal, Portland, OR (US); Nicolas Ramirez, Portland, OR (US); Matt Capozzi, Bend, OR (US); Scott Layton, Portland, OR (US)

(73) Assignee: Smith Sport Optics, Inc., Portland, OR (US)

( * ) Notice: Subject to any disclaimer, the term of this patent is extended or adjusted under 35 U.S.C. 154(b) by 152 days.

(21) Appl. No.: 16/159,316

(22) Filed: Oct. 12, 2018

(65) Prior Publication Data

US 2019/0113773 A1    Apr. 18, 2019

Related U.S. Application Data

(60) Provisional application No. 62/572,260, filed on Oct. 13, 2017.

(51) Int. Cl.
*G02C 7/08*       (2006.01)
*G02C 9/00*       (2006.01)
(Continued)

(52) U.S. Cl.
CPC ............... *G02C 9/04* (2013.01); *A61F 9/025* (2013.01); *G02C 3/003* (2013.01); *A61F 9/026* (2013.01);
(Continued)

(58) Field of Classification Search
CPC ...... A61F 9/025; A61F 9/02; A61F 2210/009; G02C 7/088; G02C 9/00; G02C 2200/02; G02C 2200/08; G02C 2200/04
(Continued)

(56) References Cited

U.S. PATENT DOCUMENTS 2,508,870 A    5/1950  Splaine
3,484,156 A    12/1969 Militello
(Continued)

FOREIGN PATENT DOCUMENTS

CA    2539125 A1    4/2005
CA    2466402 C     12/2007
(Continued)

OTHER PUBLICATIONS

Extended European Search Report for EP application No. 18200538.9 dated Mar. 7, 2019, pp. all.
(Continued)

*Primary Examiner* — Mahidere S Sahle
(74) *Attorney, Agent, or Firm* — Dorsey & Whitney LLP

(57) ABSTRACT

A goggle may include a goggle frame, a lens assembly magnetically coupled to the goggle frame, and first and second retention features securing the lens assembly to the goggle frame at first and second locations, respectively, to resist decoupling of the lens assembly from the goggle frame. The lens assembly may be removable from the goggle frame by actuating only one of the first retention feature or the second retention feature. A method of removing a lens assembly from a goggle frame may include actuating a first latch securing the lens assembly to the goggle frame; after actuating the first latch, pivoting the lens assembly away from the goggle frame about a second latch securing the lens assembly to the goggle frame; and after pivoting the lens assembly, laterally translating the lens assembly away from the second latch without actuating the second latch.

27 Claims, 20 Drawing Sheets

(51) Int. Cl.
 *G02C 9/04* (2006.01)
 *A61F 9/02* (2006.01)
 *G02C 3/00* (2006.01)

(52) U.S. Cl.
 CPC . *A61F 2210/009* (2013.01); *A61F 2220/0025* (2013.01); *G02C 2200/02* (2013.01); *G02C 2200/06* (2013.01); *G02C 2200/08* (2013.01)

(58) Field of Classification Search
 USPC .......... 351/47, 57, 86, 90, 96, 103, 106, 178
 See application file for complete search history.

(56) References Cited

U.S. PATENT DOCUMENTS

| | | |
|---|---|---|
| 4,699,479 A | 10/1987 | Metcalfe |
| 4,730,915 A | 3/1988 | Jannard |
| 4,878,749 A | 11/1989 | Mcgee |
| 4,968,129 A | 11/1990 | Grendol |
| 4,998,815 A | 3/1991 | Lin |
| 5,013,145 A | 5/1991 | Croll |
| 5,452,029 A | 9/1995 | Yang |
| 5,489,953 A | 2/1996 | Griffith |
| 5,532,767 A | 7/1996 | Pleune et al. |
| D377,036 S | 12/1996 | Leonardi |
| 5,594,511 A | 1/1997 | Lin |
| 5,703,669 A | 12/1997 | Park |
| D419,166 S | 1/2000 | Wiedner |
| 6,053,611 A | 4/2000 | Ku |
| D424,080 S | 5/2000 | Hall et al. |
| D428,039 S | 7/2000 | Thixton |
| 6,098,207 A | 8/2000 | Burtin |
| 6,120,144 A | 9/2000 | Park |
| 6,139,142 A | 10/2000 | Zelman |
| 6,149,269 A | 11/2000 | Madison |
| 6,253,388 B1 | 7/2001 | Lando |
| 6,402,318 B1 | 6/2002 | Xiao |
| 6,505,932 B2 | 1/2003 | Xiao |
| D477,010 S | 7/2003 | Moritz et al. |
| 6,585,370 B2 | 7/2003 | Zelman |
| 6,601,953 B1 | 8/2003 | Xiao |
| 6,695,448 B2 | 2/2004 | Xiao |
| 6,755,522 B1 | 6/2004 | Strenk |
| 6,764,175 B1 | 7/2004 | Chen |
| 6,866,385 B2 | 3/2005 | Madison et al. |
| 6,926,402 B1 | 8/2005 | Chen et al. |
| 6,942,337 B2 | 9/2005 | Zelman |
| 6,964,067 B1 | 11/2005 | Hartman |
| D515,615 S | 2/2006 | Fecteau et al. |
| 7,029,114 B2 | 4/2006 | Smith |
| 7,036,926 B2 | 5/2006 | Xiao |
| 7,040,749 B2 | 5/2006 | Smith |
| 7,040,751 B2 | 5/2006 | Madison |
| 7,097,299 B2 | 8/2006 | Zelman |
| 7,207,673 B1 | 4/2007 | Ho |
| 7,237,891 B2 | 7/2007 | Min |
| 7,241,007 B2 | 7/2007 | Cody et al. |
| D548,251 S | 8/2007 | Broersma |
| 7,347,545 B1 | 3/2008 | Jannard et al. |
| 7,370,961 B2 | 5/2008 | Lerner et al. |
| 7,431,453 B2 | 10/2008 | Hogan |
| 7,520,605 B1 | 4/2009 | Chen |
| 7,537,336 B2 | 5/2009 | Zelman |
| 7,568,797 B2 | 8/2009 | Hibbs, Jr. |
| 7,594,723 B2 | 9/2009 | Jannard et al. |
| D606,112 S | 12/2009 | Markovitz et al. |
| 7,661,815 B2 | 2/2010 | Lipawsky |
| 7,744,213 B2 | 6/2010 | Jannard et al. |
| 7,771,044 B2 | 8/2010 | Madison |
| D629,034 S | 12/2010 | McNeal et al. |
| D640,724 S | 6/2011 | Goodman et al. |
| 8,025,396 B1 | 9/2011 | Power |
| D649,577 S | 11/2011 | Goodman et al. |
| 8,092,007 B2 | 1/2012 | DiChiara |
| D653,686 S | 2/2012 | Tobia |
| D657,812 S | 4/2012 | Li |
| D670,753 S | 11/2012 | Chen |
| 8,469,510 B2 | 6/2013 | Beleby et al. |
| 8,480,226 B2 | 7/2013 | Ifergan |
| D695,335 S | 12/2013 | Goodman et al. |
| D695,818 S | 12/2013 | Laperriere et al. |
| 8,641,188 B2 | 2/2014 | DiChiara |
| 8,661,562 B2 | 3/2014 | Calilung et al. |
| 8,668,330 B2 | 3/2014 | Reyes et al. |
| 8,746,877 B2 | 6/2014 | Belbey et al. |
| D711,960 S | 8/2014 | Mage et al. |
| D711,961 S | 8/2014 | Arnette |
| 8,800,067 B2 | 8/2014 | Saylor et al. |
| D714,378 S | 9/2014 | Sandor |
| 8,832,904 B2 | 9/2014 | Kidouchim |
| D715,350 S | 10/2014 | Moritz et al. |
| D718,369 S | 11/2014 | Janavicius et al. |
| D723,094 S | 2/2015 | Chen |
| D725,690 S | 3/2015 | Garfias |
| D729,303 S | 5/2015 | Laperriere et al. |
| D730,430 S | 5/2015 | Tanguy et al. |
| 9,104,043 B2 | 8/2015 | Crescenzi et al. |
| D741,323 S | 10/2015 | Bosveld et al. |
| D741,858 S | 10/2015 | Bosveld et al. |
| 9,192,519 B2 | 11/2015 | Tobia |
| 9,220,633 B2 | 12/2015 | Tobia |
| 9,241,833 B2 | 1/2016 | Cater et al. |
| 9,341,865 B2 | 5/2016 | Sheldon et al. |
| D769,350 S | 10/2016 | Orzeck et al. |
| 9,463,117 B2 | 10/2016 | Belbey et al. |
| D774,123 S | 12/2016 | Chae |
| D776,187 S | 1/2017 | Tappeiner et al. |
| D777,826 S | 1/2017 | Shin |
| D783,697 S | 4/2017 | Chae |
| D785,699 S | 5/2017 | Chen |
| D805,576 S | 12/2017 | Garfias |
| D811,664 S | 2/2018 | Knauer et al. |
| 9,943,444 B2 | 4/2018 | Kilduff et al. |
| D818,031 S | 5/2018 | Garfias |
| D821,037 S | 6/2018 | Wallis |
| D827,007 S | 8/2018 | Garfias |
| D827,208 S | 8/2018 | Baudet |
| D827,690 S | 9/2018 | Shin |
| D828,866 S | 9/2018 | Yoo et al. |
| D834,087 S | 11/2018 | Yoo et al. |
| D868,878 S | 12/2019 | Langenwalter et al. |
| 2004/0046929 A1 | 3/2004 | Wu |
| 2004/0141146 A1 | 7/2004 | Blanchette et al. |
| 2006/0005299 A1 | 1/2006 | Lerner |
| 2007/0058130 A1 | 3/2007 | Babineau et al. |
| 2007/0153230 A1 | 7/2007 | Musal et al. |
| 2011/0051074 A1 | 3/2011 | Arnell |
| 2011/0199680 A1 | 8/2011 | Saylor et al. |
| 2011/0273661 A1 | 11/2011 | Lin |
| 2012/0038878 A1 | 2/2012 | Echevarria |
| 2013/0077042 A1 | 3/2013 | Calilung et al. |
| 2013/0104300 A1 | 5/2013 | Park |
| 2013/0185849 A1 | 7/2013 | Laughlin et al. |
| 2014/0157496 A1 | 6/2014 | Ginther et al. |
| 2014/0300854 A1 | 10/2014 | Fox |
| 2015/0121611 A1 | 5/2015 | Isabelle |
| 2015/0245675 A1 | 9/2015 | Chinquee |
| 2016/0026004 A1 | 1/2016 | Sheldon et al. |
| 2016/0106592 A1 | 4/2016 | Tobia |
| 2016/0331591 A1 | 11/2016 | Kilduff et al. |
| 2017/0128267 A1 | 5/2017 | Rees et al. |
| 2020/0142218 A1 | 5/2020 | Mcneal et al. |

FOREIGN PATENT DOCUMENTS

| | | |
|---|---|---|
| CN | 104114132 A | 10/2014 |
| CN | 206080839 U | 4/2017 |
| CN | 106618852 A | 5/2017 |
| CN | 2006261719 U | 6/2017 |
| EP | 0588215 A1 | 3/1994 |
| EP | 1127290 A1 | 8/2001 |
| GB | 2281635 A | 3/1995 |
| WO | 941481 A1 | 11/1997 |
| WO | 2018011527 A1 | 1/2016 |

(56) References Cited

FOREIGN PATENT DOCUMENTS

OTHER PUBLICATIONS

U.S. Appl. No. 29/622,139, entitled "Goggle" filed Oct. 13, 2017.
Office Action for CA Application No. 3,020,818, dated Aug. 20, 2019, 4 pgs.
U.S. Appl. No. 16/672,358 titled "Goggle Lens With Compound Curvature for Downward Field of View Enhancement" filed Nov. 1, 2019.

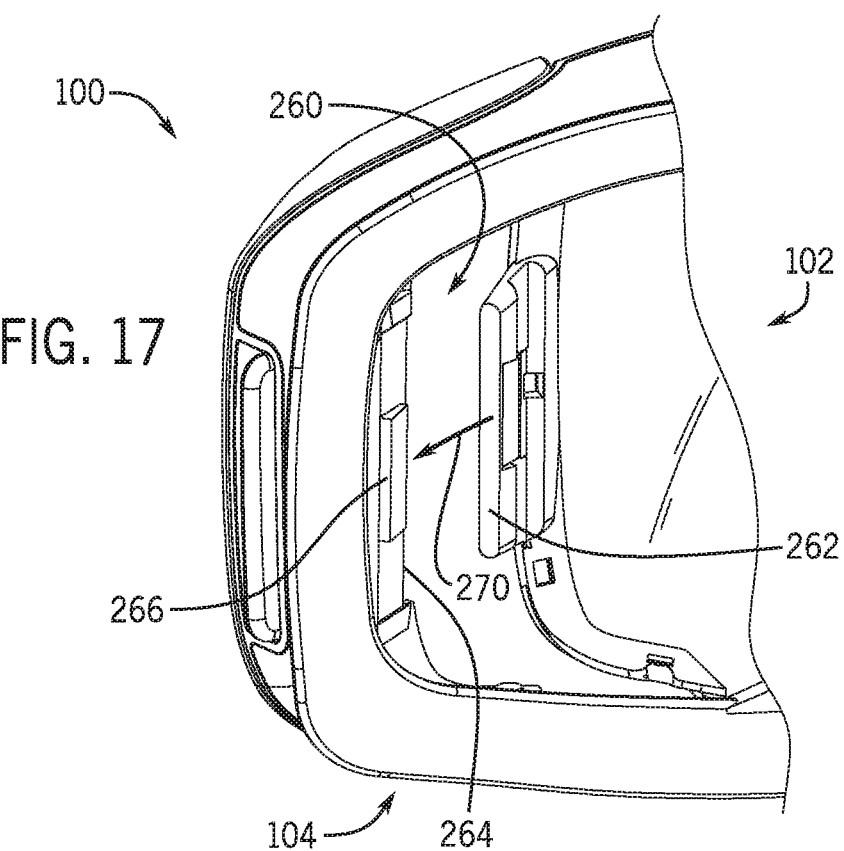
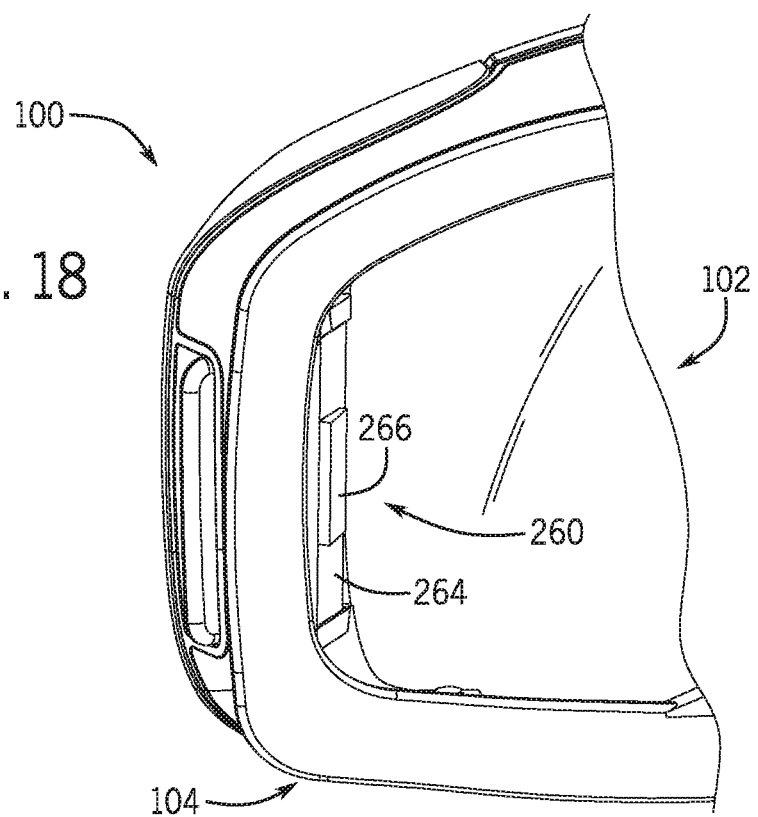

GOGGLE WITH REPLACEABLE LENS

CROSS-REFERENCE TO RELATED APPLICATION(S)

This application claims priority to U.S. Provisional Application No. 62/572,260 filed Oct. 13, 2017, which is incorporated herein by reference, in its entirety, for any purpose.

BACKGROUND

Goggles with replaceable lenses typically include a frame and one or more removable lenses. The frame may be equipped with a mechanism for attachment of the lens. In some goggles, the lens is attached to the frame with magnets. However, in existing goggles of this kind, the lens may be easily dislodged from the frame. Additionally or alternatively, in existing goggles, removal of the lens may be unduly complex or cumbersome for a user, or may have other deficiencies which result in a suboptimal user experience. For these reasons or other reasons, improvements in goggles with removable lenses may be desired.

BRIEF DESCRIPTION OF THE DRAWINGS

The description will be more fully understood with reference to the following figures in which components may not be drawn to scale, which are presented as various embodiments of the eyewear and eyewear components described herein and should not be construed as a complete depiction of the scope of the present disclosure.

FIG. 17 is a partial rear view of the goggle of FIG. 16.

FIG. 18 is a partial rear view of the goggle of FIG. 16 with the lens assembly coupled to the goggle frame.

DETAILED DESCRIPTION

Examples of goggles with removable lenses are described. In some examples, the goggle may include a first retention feature (e.g., magnets) that couple a lens assembly to a goggle frame. To limit inadvertent decoupling of the lens assembly from the goggle frame, the goggle may include a second retention feature (e.g., a latch mechanism) for securing the lens assembly to the goggle frame. In some embodiments, the latch mechanism may include latch components attached to the lens assembly and the goggle frame for securing the lens assembly to the goggle frame. In some embodiments, the latch components may engage mechanically for mechanically securing the lens assembly to the goggle frame. In some embodiments, the latch mechanism may include one or more magnetic elements (e.g., magnets) for securing the lens assembly to the goggle frame. The latch mechanism may include at least one actuator for manipulation by the user to release and/or engage the latch, and at least one tab that includes engagement feature(s) which cooperate with respective engagement feature(s) on the actuatable component to engage the latch. The actuator may be coupled to the goggle frame or the lens frame. In some embodiments, the actuator is coupled to the goggle frame, for example behind an outrigger so as to at least partially conceal the actuator from view and provide a more aesthetically pleasing look of the goggle.

Figure 1:
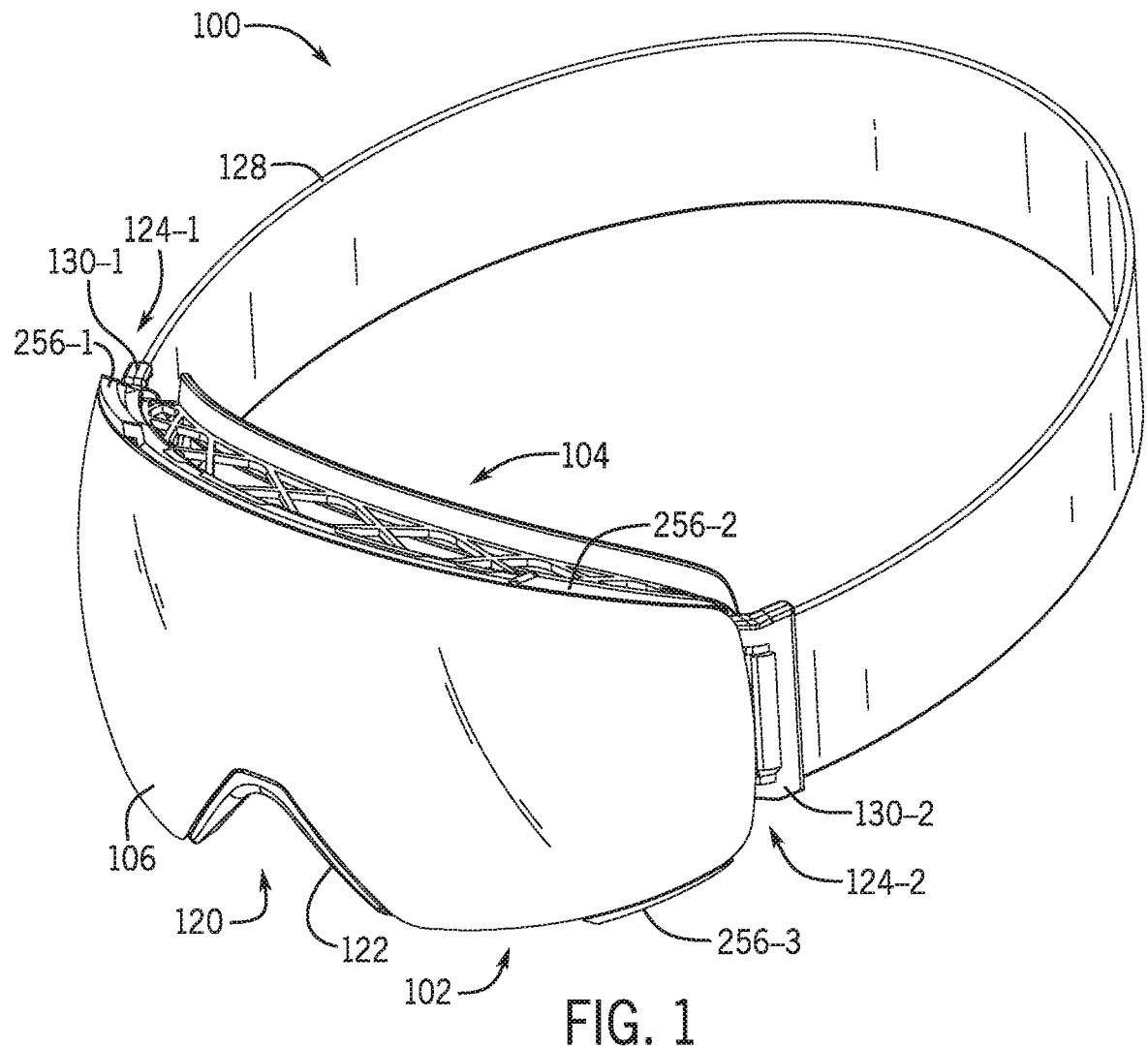
FIG. 1 is an isometric view of a goggle in accordance with some examples of the present disclosure.

As shown in FIG. 1, an example goggle 100 includes a lens assembly 102 removably coupled to a goggle frame 104. The goggle 100 may be of a shield-type design including a single or unitary outer lens 106, which may be configured to extend in the field of view of both the left and right eyes of the user when worn. The outer lens 106 may be formed from a single lens blank and may thus be devoid of any seams or other discontinuities in the lens. The outer lens 106 may be made from polycarbonate (PC), acrylic, or other materials which can provide suitable optical qualities (e.g., optical clarity) to the optical portion of the eyewear. The outer lens 106 may be rimless or frameless in that a perimeter of the lens 106 is not substantially enclosed by a frame, as illustrated in FIG. 1. These features may provide a larger unobstructed field of view through the outer lens 106.

Figure 14:
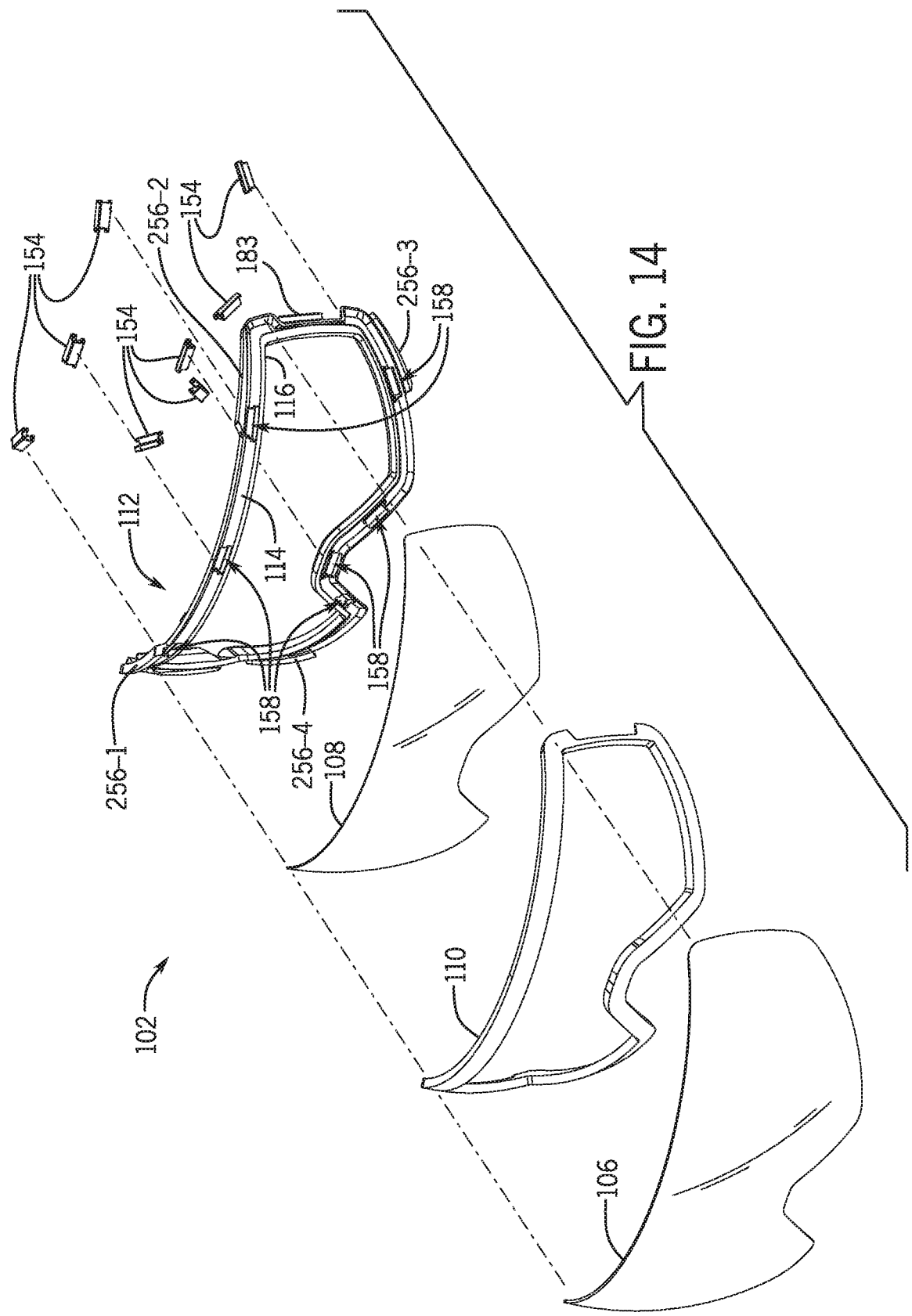
FIG. 14 is an exploded isometric view of a lens assembly of the goggle of FIG. 1.

In some embodiments, the lens assembly 102 may include a dual-lens structure. For example, as illustrated in FIG. 14, the lens assembly 102 may include outer lens 106 and inner lens 108. The lenses 106, 108 may have a generally arcuate shape, such as cylindrical, spherical or another type of arcuate shape. The lenses 106, 108 may comprise one or more compounds and/or coatings configured to impart light transmittance characteristics as may be desired or suitable for a particular application. For example, the lenses 106, 108 may include one or more compounds or coatings, which configure the lenses 106, 108 into a tinted lens, a polarized lens, a scratch resistant lens, or combinations thereof. Additionally or alternatively, the lenses 106, 108 may be formed from a projectile- or shatter-resistant material selected to meet one or more ballistic safety standards. The lenses 106, 108 may have a front or outward-facing surface (i.e. the side of the lenses, which is farthest away from the user's face when the eyewear is worn) and a rear or inward-facing surface (i.e. the side of the lens, which is closest to the user's face when the eyewear is worn). Compounds and/or coatings, such as for tinting the lenses 106, 108, may be laminated in the body of the lenses 106, 108 and/or applied to either of the rear or front sides of the lenses 106, 108.

Referring still to FIG. 14, the lens assembly 102 may include a spacer 110 (e.g., a foam spacer) that attaches the outer and inner lenses 106, 108 together. The spacer 110 may be positioned at least partially between the outer lens 106 and the inner lens 108, and may extend along a peripheral portion of the outer lens 106 and the inner lens 108 so as to provide a large unobstructed field of view through the outer lens 106 and the inner lens 108. The spacer 110 may include adhesive on both of its sides (i.e., its front and rear surfaces) to adhere the outer lens 106 to the inner lens 108. For example, the spacer 110 may be implemented using a double-sided adhesive foam tape.

With continued reference to FIG. 14, the lens assembly 102 may include a lens frame 112 configured for removably coupling the lens assembly to the goggle frame 104. The lens frame 112 may support the inner lens 108 and/or the spacer 110. As shown in the illustrated embodiment, the lens frame 112 may define a seat 114 that receives and supports the spacer 110. A rear surface of the spacer 110 may abut against the seat 114 when the lens assembly 102 is assembled, and adhesive applied to the rear surface of the spacer 110 may adhere the spacer 110 to the lens frame 112. In some embodiments, the lens frame 112 is formed of polycarbonate, and may be molded. The lens frame 112 may thus be relatively more rigid as compared to the relatively softer portions of the goggle frame 104 that are positioned conformally to the user's face.

Figure 15:
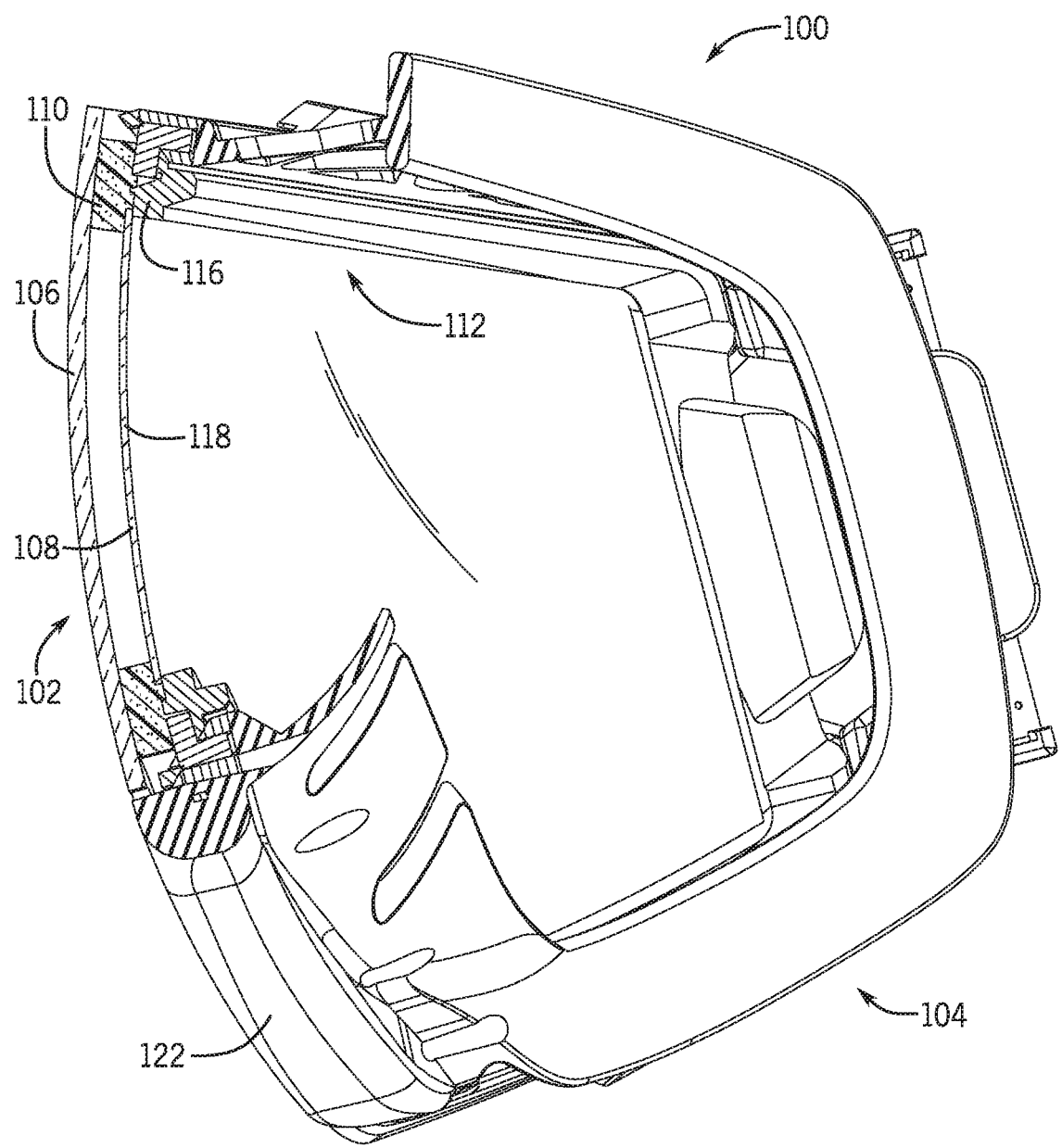
FIG. 15 is a cross-sectional view of the goggle of FIG. 1 taken along sectional line 15-15 in FIG. 8.

Referring to FIGS. 14 and 15, the lens frame 112 may be configured to extend along a peripheral portion of the inner lens 108 to restrict the inner lens 108 from delaminating or separating from the spacer 110. The inner lens 108 may be formed of a different material than the outer lens 106. For example, the inner lens 108 may be designed to be hydrophilic to inhibit fogging, which may reduce the effectiveness of the adhesive on the spacer 110. To inhibit or reduce the risk of separation of the inner lens 108 and the spacer 110, the lens frame 112 may include a lip 116 that extends interiorly from the seat 114 (see FIG. 14). The lip 116 may abut against a rear surface 118 of the inner lens 108 (see FIG. 15) around a periphery of the inner lens 108. With the spacer 110 bonded to the seat 114 of the lens frame 112 (see FIG. 14), the inner lens 108 may be captured or sandwiched between the spacer 110 and the lip 116 of the lens frame 112, thereby inhibiting separation of the inner lens 108 from the spacer 110. As illustrated in FIG. 15, the inner lens 108 may be smaller in size (e.g., height and/or thickness) than the outer lens 106.

As illustrated in FIG. 1, the goggle 100 may define a nose recess 120 (e.g., along a bottom periphery of the lens assembly 102), which may be configured to accommodate the nose of the wearer when the goggle 100 is worn. In some embodiments, a nose pad 122 may be provided at the nose recess 120. The nose pad 122 may be formed from a soft or flexible polymeric material (e.g., thermoplastic elastomer (TPE), such as a thermoplastic polyurethane (TPU) material) which may conform to the user's nose for a comfortable fit and may optionally include one or more bendable portions for improved adjustability. The nose pad 122 may form part of the goggle frame 104 (see FIG. 13), which may also be at least partially formed of a TPE, or may connect directly to the lens assembly 102 at the recess 120. In some examples, the nose pad 122 may be removably attached to the lens assembly 102 or the goggle frame 104, such as to enable replacement of the nose pad 122.

The goggle 100 may include first and second opposite end portions 124-1, 124-2. A strap 128 (such as an elastic headband) may be attached to each of the first and second end portions 124-1, 124-2 via first and second outriggers 130-1, 130-2, respectively (see FIGS. 1 and 8). Each outrigger 130-1, 130-2 may be pivotally coupled to the goggle frame 104 to provide a relatively customized fit of the strap 128 around a front portion of a wearer's head.

In some embodiments, the lens assembly 102 may be a magnetically coupled to the goggle frame 104. The lens assembly 102 and the goggle frame 104 may include magnetic materials (e.g., a permanent magnet such as a rare earth magnet, or ferromagnetic material such as iron or steel) for removably coupling the lens assembly 102 to the goggle frame 104. In some embodiments, the magnetic materials may have one or more surfaces exposed (e.g., the facing surfaces of the magnets). The magnetic materials may be substantially enclosed (e.g., except for one side of the magnetic material being at least partially exposed) in pockets formed within the lens assembly and the goggle frame. The magnetic materials may be attached to opposing (e.g., facing) sides of the lens assembly 102 and the goggle frame 104 to urge the lens assembly 102 towards the goggle frame 104. The magnetic attraction between the magnetic materials on the lens assembly 102 and the goggle frame 104 may provide a centering function (e.g., resulting from the magnetic materials natural tendency to axially align their respective fields to one another), which may facilitate alignment of the lens assembly 102 to the goggle frame 104.

Referring to FIGS. 2 through 5, the goggle frame 104 may include magnetic materials for magnetic coupling with corresponding magnetic materials on the lens assembly 102. For example, the goggle frame 104 may include magnets 134 exposed along an angled surface 136 of the goggle frame 104. The magnets 134 may be arranged along a lower portion of the goggle frame 104 (such as generally beneath a wearer's eyes and adjacent the wearer's nose) and along an upper portion of the goggle frame 104 (such as adjacent a wearer's forehead). Several magnets 134 may be arranged adjacent the nose pad 122. In the illustrated embodiment, the goggle frame 104 includes eight magnets 134, but in other embodiments the goggle frame 104 may include more or less than eight magnets 134. The magnets 134 may include an exposed surface that is substantially flush with the angled surface 136, which may be angled inward and rearward toward a center of the goggle frame 104 to facilitate alignment of the lens assembly 102 with the goggle frame 104. The magnets 134 may be oriented at about a forty-five degree angle (e.g., forty-five degrees plus or minus thirty degrees) to facilitate alignment of the lens assembly 102 with the goggle frame 104. In some embodiments, the angled surface 136 and the magnets 134 are oriented at a forty-five degree angle relative to a plane defined by the curvature of the outer lens 106 to facilitate alignment of the lens assembly 102 with the goggle frame 104. In other embodiments, different arrangement (e.g., orientation) of the magnets with respect to the surface 136 may be used.

Figure 13:
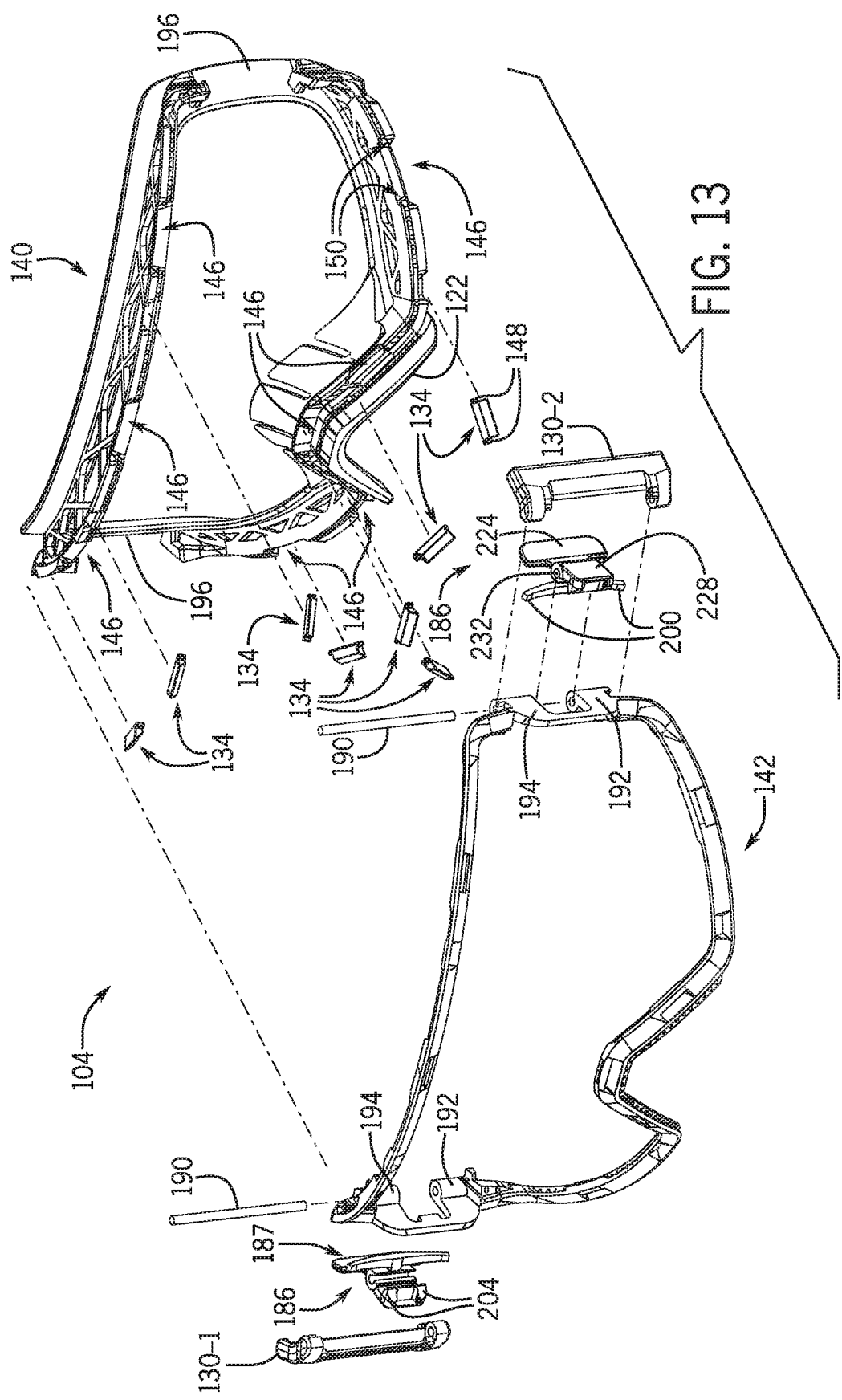
FIG. 13 is an exploded isometric view of a goggle frame of the goggle of FIG. 1.

Referring to FIG. 13, the goggle frame 104 may include a face gasket and an interface component for interfacing with the removable lens assembly. The face gasket may be provided by one or more resiliently deformable components, which are configured to placed conformally to the user's face. In the embodiment in FIG. 13, the face gasket is provided by a frame ring 140. In some embodiments, e.g., as shown in FIG. 13, the interface component is implemented as an overmold component or material 142. The overmold material 142 may be formed of a relatively hard or rigid material (e.g., nylon) to form an interface component that provides a structural base for interfacing with the lens frame 112. The face gasket (e.g., frame ring 140) of the goggle frame 104 may be formed of a softer material (e.g., thermoplastic polyurethane (TPU)) for conformally interfacing with the wearer's face. In some embodiments, the frame ring 140, which may be formed from the relatively more flexible material (e.g., IPU) for example by an injection molding process, may be overmolded by the relatively more rigid material (e.g., nylon) in an overmold process during which the interface component is shaped or formed while being joined to the frame ring. In other embodiments, the interface components) may be formed first and the overmolded by the face gasket material.

In some embodiments, the magnets 134 are inserted into pockets 146 defined in the frame ring 140, and then the frame ring 140 is overmolded by the overmold material 142, thereby effectively molding the magnets 134 into the goggle frame 104. The magnets 134 may be attached to the frame ring 140, such that the frame ring 140 counteracts the magnetic force imposed on the magnets 134 by the lens assembly 102 to ensure the magnets 134 are not pulled out of the goggle frame 104 during decoupling of the lens assembly 102 from the goggle frame 104. For example, as illustrated in FIG. 13, the magnets 134 may include wings 148 extending from opposing ends of the magnets 134, and the wings 148 may be received within slots 150 formed in the frame ring 140 at opposing ends of the pockets 146. The overmold material 142 may cover at least a front portion of the frame ring 140 and at least a portion of the magnets 134 to lock the magnets 134 in place (e.g., restrict the wings 148 of the magnets 134 from sliding out of the slots 150 in the frame ring 140). At least a portion of a front surface of the magnets 134 may be exposed through the overmold material 142 to facilitate magnetic coupling of the magnets 134 with the lens assembly 102.

Figure 3:
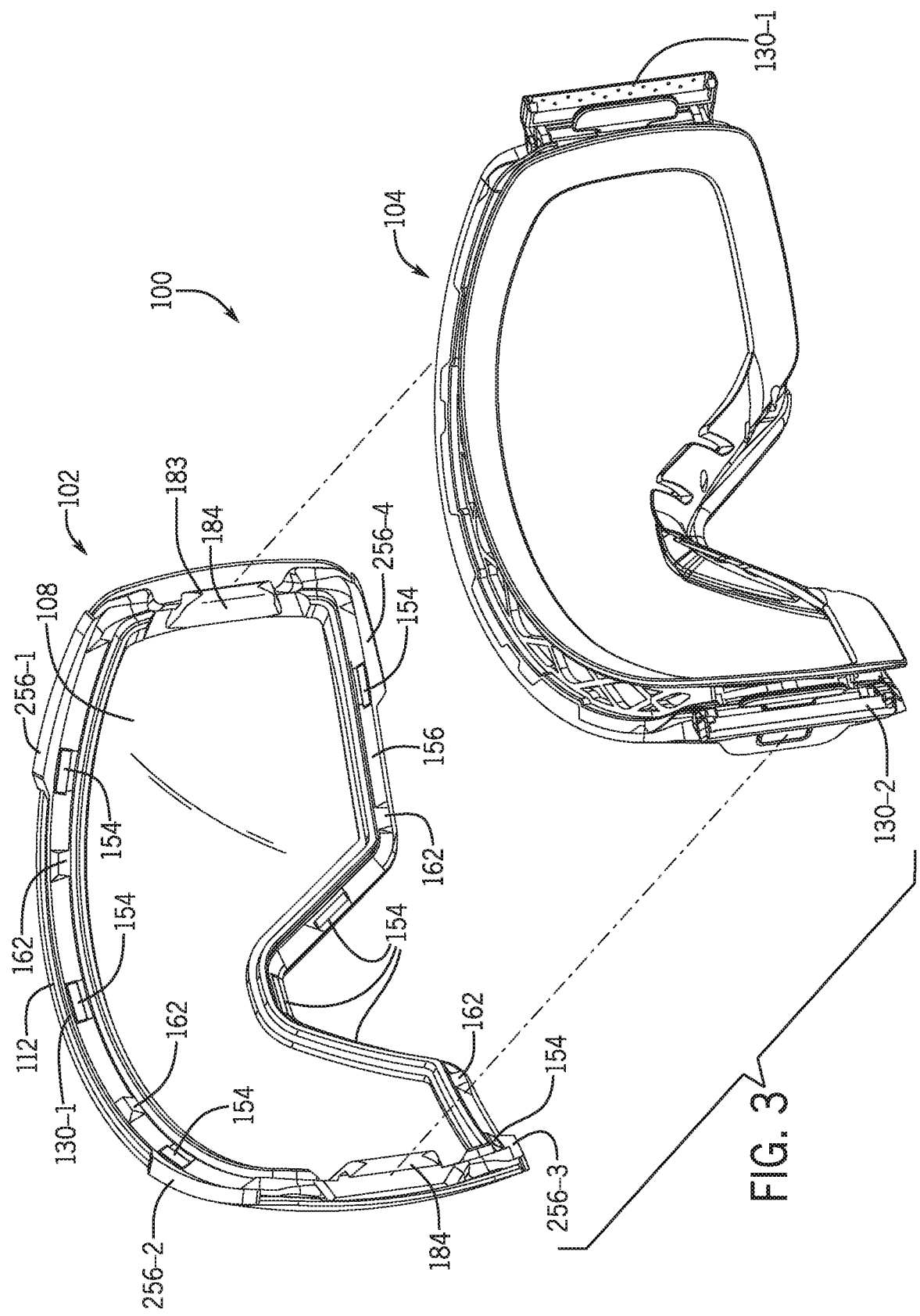
FIG. 3 is a partially exploded rear isometric view of the goggle of FIG. 1.
Figure 4:
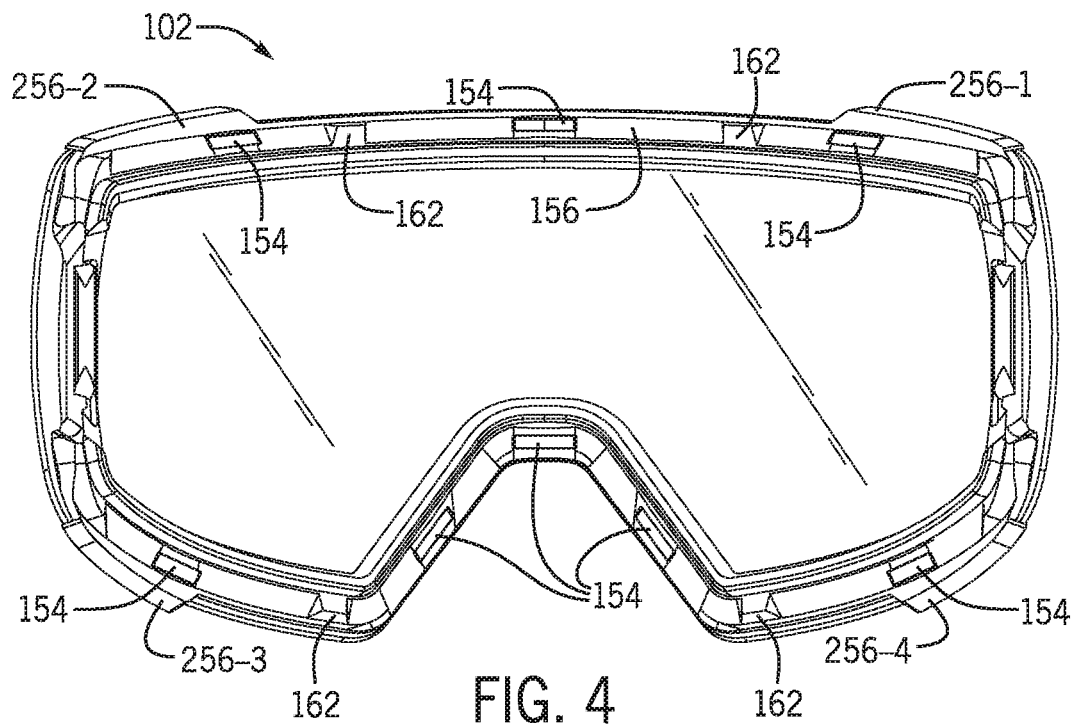
FIG. 4 is a rear view of a lens assembly of the goggle of FIG. 1.

Referring to FIGS. 3 and 4, the lens assembly 102 may include magnetic materials for magnetic coupling with corresponding magnetic materials on the goggle frame 104. For example, the lens assembly 102 may include magnets 154 exposed along an angled surface 156 of the lens assembly 102. The magnets 154 may be arranged at corresponding locations to the magnets 134 of the goggle frame 104, and may include opposing polarities to the magnets 134 such that the magnets 134, 154 are attracted to each other. The magnets 154 may include an exposed surface that is substantially flush with the angled surface 156, which may be angled at a corresponding angle to the angled surface 136 of the goggle frame 104 to facilitate alignment of the lens assembly 102 with the goggle frame 104. The magnets 154 may be oriented at about a forty-five degree angle (e.g., forty-five degrees plus or minus thirty degrees) to facilitate alignment of the lens assembly 102 with the goggle frame 104. In some embodiments, the angled surface 156 and the magnets 154 are oriented at a forty-five degree angle relative to a plane defined by the curvature of the inner lens 108 to facilitate alignment of the lens assembly 102 with the goggle frame 104. As illustrated in FIG. 14, the magnets 154 may be received in pockets 158 defined in the lens frame 112. The magnets 154 may only be inserted into the pockets 158 from a front side of the lens frame 112, such that the lens frame 112 inhibits the magnets 154 from being pulled out of the lens assembly 102 during decoupling of the lens assembly 102 from the goggle frame 104.

Figure 2:
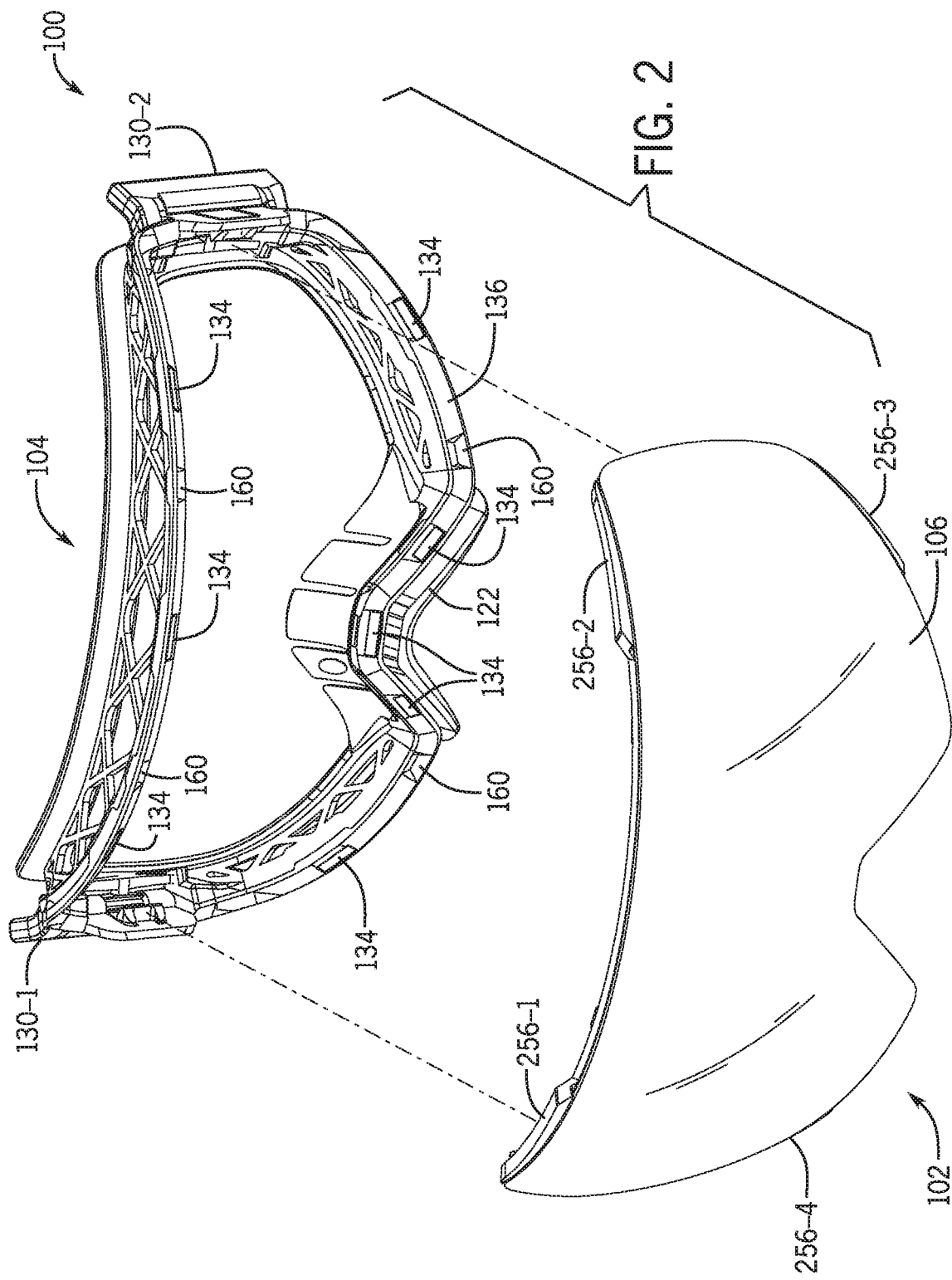
FIG. 2 is a partially exploded front isometric view of the goggle of FIG. 1.
Figure 5:
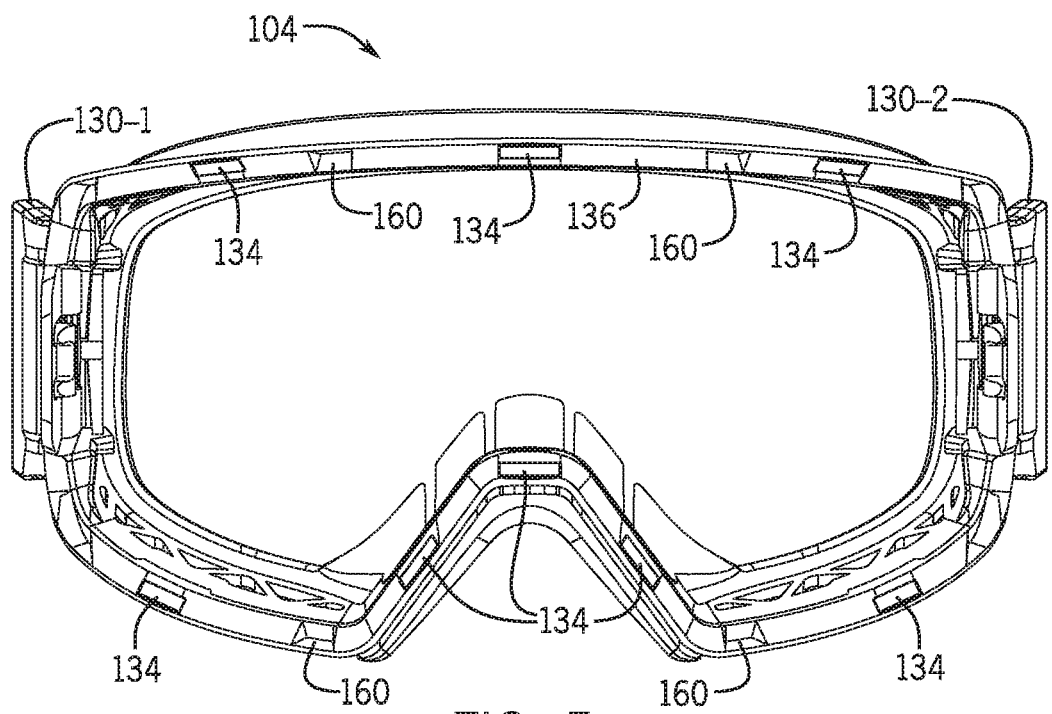
FIG. 5 is a front view of a goggle frame of the goggle of FIG. 1.

As previously described, positioning and/or alignment of the lens assembly 102 relative to the goggle frame 104 may be achieved substantially by the shape and/or contours of the corresponding contact surfaces of the lens assembly 102 and the goggle frame 104, which in the illustrated embodiment is defined in part by the shape and wall contours of the peripheral rim of the lens assembly 102 and the goggle frame 104. Additionally or alternatively, positioning and/or alignment of the lens assembly 102 with respect to the goggle frame 104 may be aided by the automatic centering of the magnetic interaction between the lens assembly 102 and the goggle frame 104. In some embodiments, the lens assembly 102 and the goggle frame 104 may include corresponding alignment features to facilitate alignment of the lens assembly 102 to the goggle frame 104. For example, as illustrated in FIGS. 2-5, the lens assembly 102 and the goggle frame 104 may include corresponding extensions and recesses to facilitate alignment of the lens assembly 102 and the goggle frame 104. Referring to FIGS. 2 and 5, the goggle frame 104 may include recesses 160 defined in the angled surface 136. The recesses 160 may be arranged between adjacent magnets 134. Referring to FIGS. 3 and 4, the lens assembly 102 may include extensions 162 protruding from the angled surface 156, and the extensions 162 may correspond to the locations of the recesses 160 defined in the goggle frame 104. The extensions 162 may be received in the recesses 160 when the lens assembly 102 is properly aligned with the goggle frame 104, and, when received in the recesses 160, the extensions 162 may restrict lateral movement of the lens assembly 102 relative to the goggle frame 104. In other embodiments, the recesses 160 may be defined in the lens assembly 102, and the extensions 162 may be formed on the goggle frame 104. In other embodiments, the length of recesses 160 and extensions 162 may be extended. The recesses 160 may extend along a length of the angled surface 136 such that they substantially span a distance between adjacent magnets 134 along the angled surface 136. The extensions 162 may extend along a length of angled surface 156 such that they substantially span a distance between adjacent magnets 154, corresponding to the locations and lengths of recesses 160. Extending the lengths of the recesses 160 and extensions 162 may further facilitate alignment of the lens assembly 102 and the goggle frame 104.

Magnetic force acting between magnetic materials positioned on opposing faces of the lens assembly 102 and the goggle frame 104 may resist separation of the lens assembly 102 from the goggle frame 104. In some examples, the lens assembly 102 may additionally or alternatively be mechanically coupled to the goggle frame 104. For example, the goggle 100 may include two or more retention features for mechanically interlocking the lens assembly 102 to the goggle frame 104. In some examples, the lens assembly 102 may include latch components (e.g., protrusion, hooks, or other surface or edge features which may be operably connected to levers or other actuators for actuating the same) which may be configured to interlock with corresponding latch components of the goggle frame 104 such as to resist separation of the lens assembly 102 from the goggle frame 104.

The two or more retention features of the goggle 100 may prevent inadvertent separation of the lens assembly 102 from the goggle frame 104. For example, the two or more retention features may prevent the lens assembly 102 from being accidentally detached from the goggle frame 104 when the goggle 100 is being worn. In the absence of the retention features described herein (e.g., latches), the magnetic force between the lens assembly 102 and the goggle frame 104 may be insufficient, and the lens assembly 102 may pop off or disengage the goggle frame 104, which would be undesirable. Using magnets that provide a sufficiently strong magnetic field to resist inadvertent detachment may not be a practical solution because this would make coupling or decoupling of the lens assembly 102 by the user more arduous (e.g., the user would have to apply significantly more force to remove the lens assembly 102), thus detracting from the user experience. The combination of using two or more retention features (e.g., latches) and magnetic coupling to maintain the lens assembly 102 in engagement with the goggle frame 104 in accordance with the examples disclosed herein may provide a more elegant solution.

Figure 8:
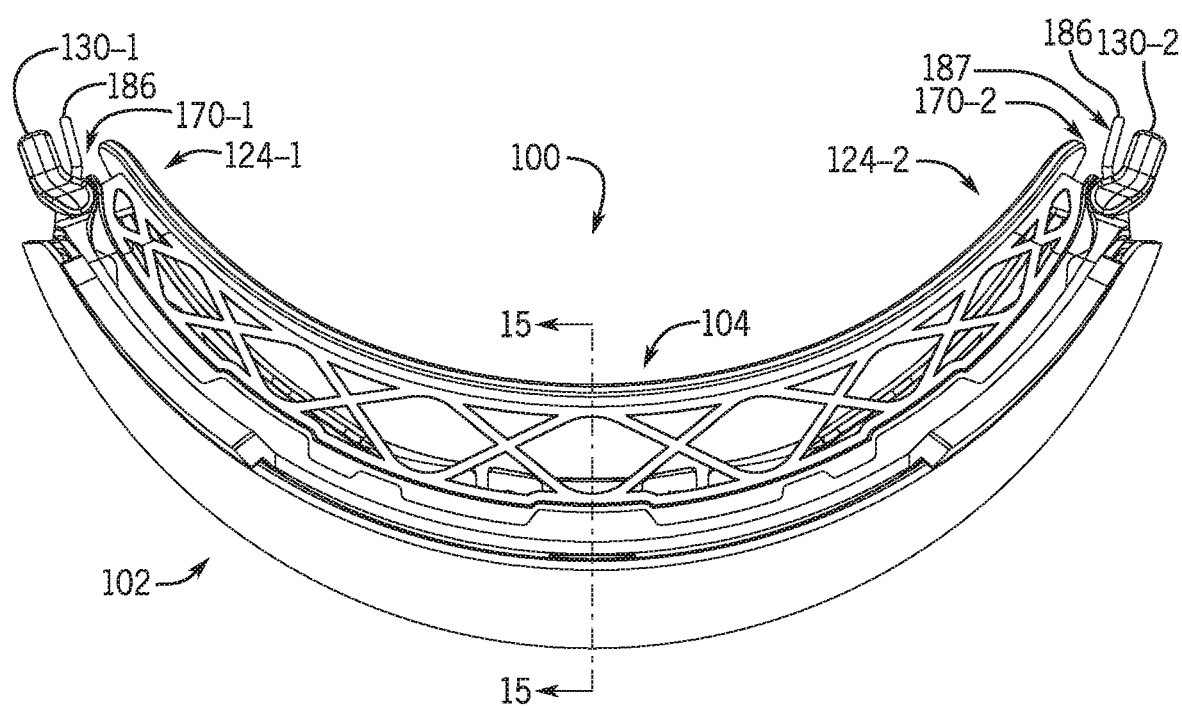
FIG. 8 is a top view of the goggle of FIG. 1.

Referring to FIG. 8, the goggle 100 may include a plurality of retention features (e.g., two or more retention features) to secure the lens assembly 102 to the goggle frame 104. For example, as illustrated in FIG. 8, the goggle 100 may include first and second retention features 170-1, 170-2 at first and second locations, respectively, to resist inadvertent decoupling of the lens assembly 102 from the goggle frame 104. The retention features 170-1, 170-2 may be positioned anywhere around the perimeter of the goggle 100 (e.g., at the sides, top, bottom, etc.). The retention features 170-1, 170-2 may be attached to the goggle 100 at various locations, for example at opposite (e.g., left and right) end portions 124-1, 124-2 of the goggle 100. As illustrated in FIG. 8, the retention features 170-1, 170-2 may be at least partially concealed by the first and second outriggers 130-1, 130-2, respectively.

Figure 9:
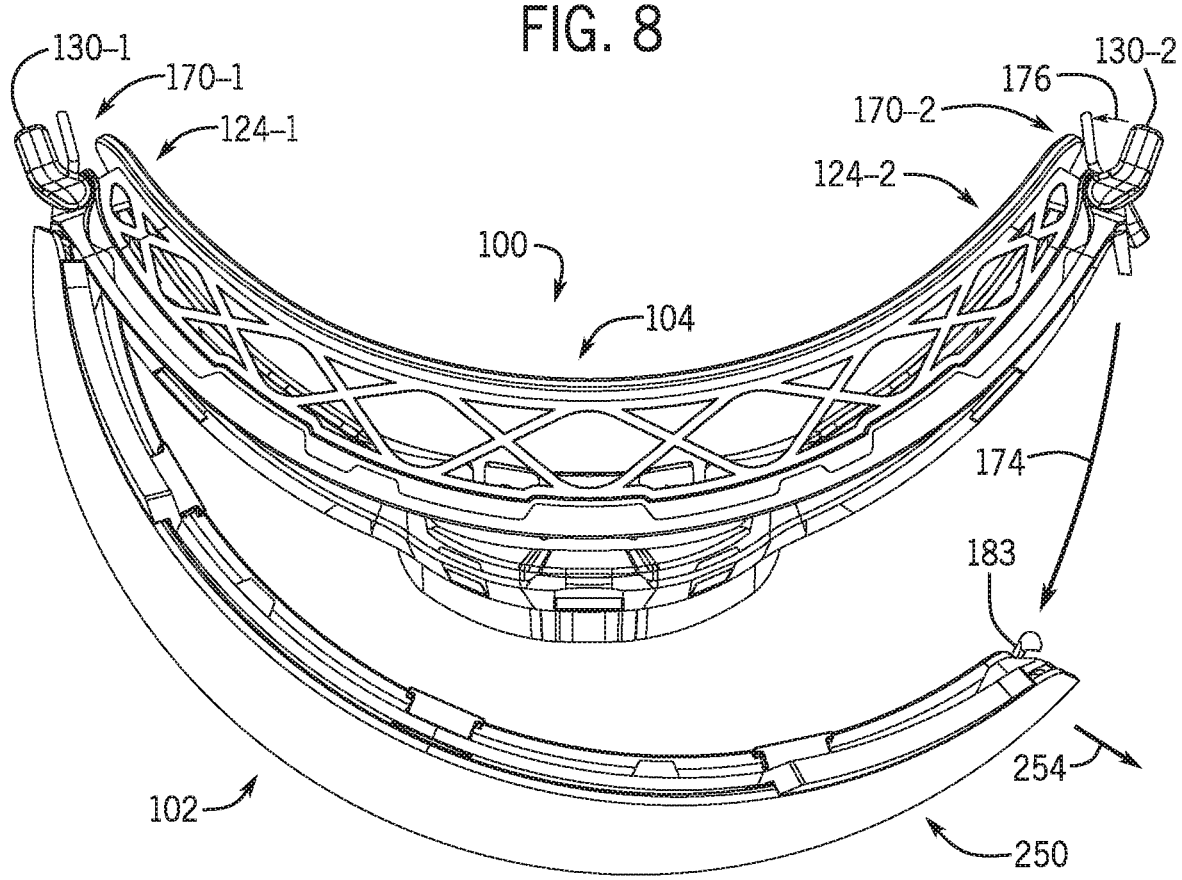
FIG. 9 is a top view of the goggle of FIG. 1 illustrating movement of a latch component on the goggle frame and of a lens assembly when decoupling or removing the lens assembly from a goggle frame.

Referring to FIG. 9, the lens assembly 102 may be removable from the goggle frame 104 by actuating only one of the first and second retention features 170-1, 170-2. For example, as illustrated in FIG. 9, actuation of one of the retention features (e.g., retention feature 170-2 in FIG. 9, see arrow 176 in FIG. 9) releases one end of the lens assembly 102 from the goggle frame 104, allowing the lens assembly 102 to be pivoted away from the goggle frame 104 (see direction arrow 174 in FIG. 9) about the other retention feature (e.g., retention feature 170-1 in FIG. 9). After pivoting the lens assembly 102, the wearer may grasp the free end of the lens assembly 102 and pull the lens assembly 102 away from the retention feature 170-1 in FIG. 9 to detach the lens assembly 102 from the goggle frame 104 without actuating the retention feature 170-1.

Figure 10:
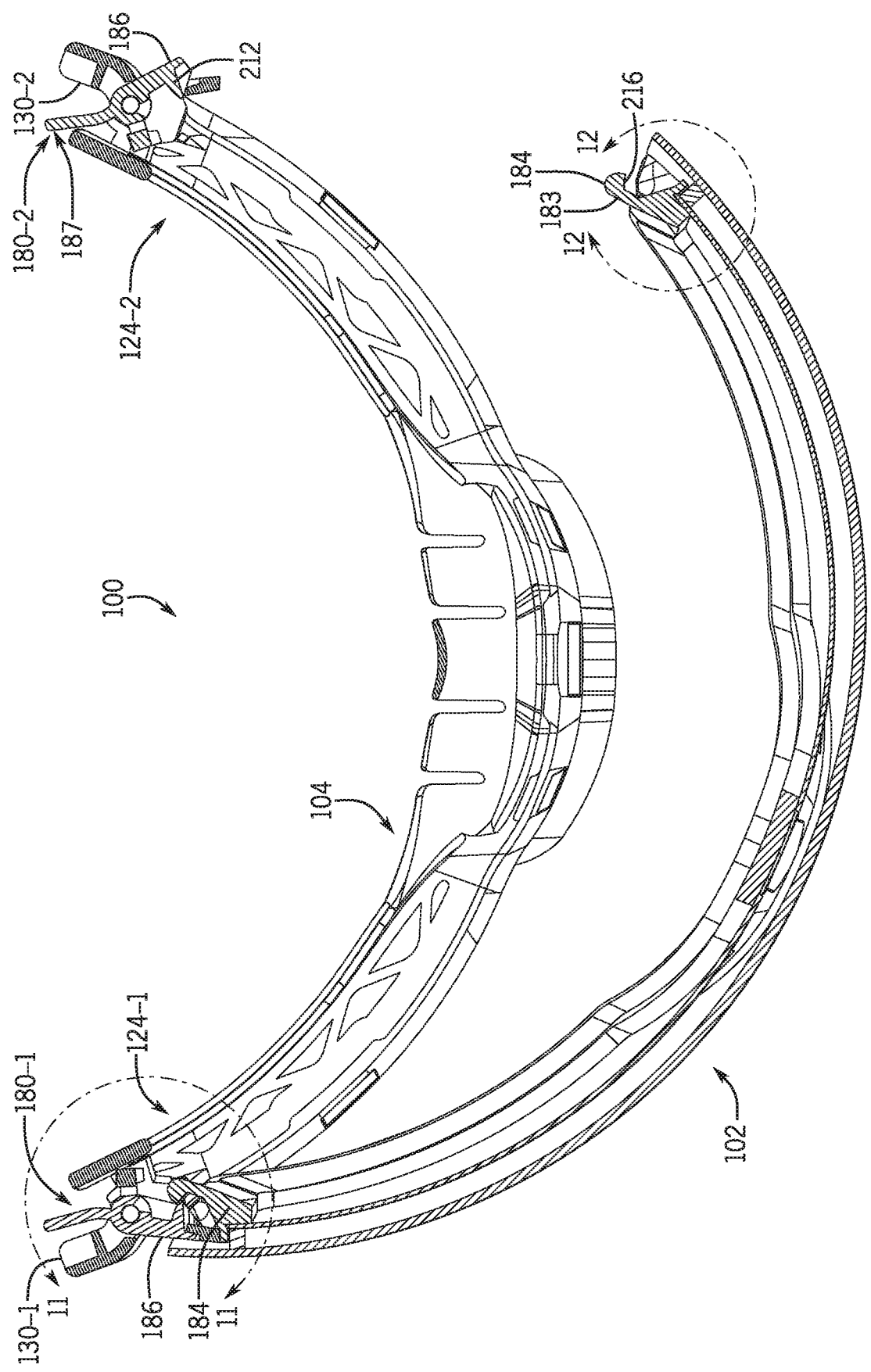
FIG. 10 is a cross-sectional view of the goggle of FIG. 11 illustrating a latch mechanism of the goggle.

In some embodiments, the retention features 170-1, 170-2 comprise latches (also referred to as latch mechanisms). For example, as illustrated in FIG. 10, the goggle 100 may include a first latch 180-1 and a second latch 180-2. The latches 180-1, 180-2 may be coupled to or proximate the end portions 124-1, 124-2, respectively, of the goggle 100. Each latch 180-1, 180-2 may include a first latch component 184 coupled to the lens assembly 102 and a second latch component 186 coupled to the goggle frame 104.

With continued reference to FIG. 10, the lens assembly 102 may include the first latch components 184 of the latches 180-1, 180-2, and each latch component 184 may be coupled to a respective end portion of the lens assembly 102. The first latch components 184 may be fixedly attached to the lens assembly 102 which generally implies that the first latch components 184 are not be intended to be removed during normal use of the goggle 100. For example, the first latch components 184 may be attached (e.g., bonded and/or mechanically secured) to the lens assembly 102 or may be formed integrally with the lens assembly 102 as a unitary structure. In the illustrated embodiment, the lens assembly 102 includes two separate latch components attached to the opposite ends (e.g., distal ends) of the lens assembly 102, although in other embodiments the lens assembly 102 may include more than two latch components.

Referring still to FIG. 10, the first latch components 184 of the latches 180-1, 180-2 may be arranged generally along the arc length direction of the lens assembly 102, which may serve aesthetic and/or utilitarian functions. In the embodiment illustrated in FIG. 10, each of the first latch components 184 extends from one of two opposite ends of the lens assembly 102 in a direction generally following the curvature of the lens assembly 102. The first latch components 184 may be arranged as an extension to the ends of the lens assembly 102 such that the first latch components 184 project at least partially from the ends of the lens assembly 102, thereby providing a slimmer form factor, which may be more appealing to the user. In some cases, the slimmer form factor may enable a more compact packaging of the lens assembly 102. In the embodiment in FIG. 10, each of the first latch components 184 extends from one of two opposite ends of the lens assembly 102 in a direction generally following the curvature of the lens assembly 102, which may facilitate connection of the lens assembly 102 to the goggle frame 104. As illustrated in FIG. 3, the first latch components 184 may extend rearward from the ends of the lens assembly 102. The first latch components 184 may be formed as tabs that are fixedly attached to the lens frame 112 and project rearward from the lens frame 112.

Figure 11:
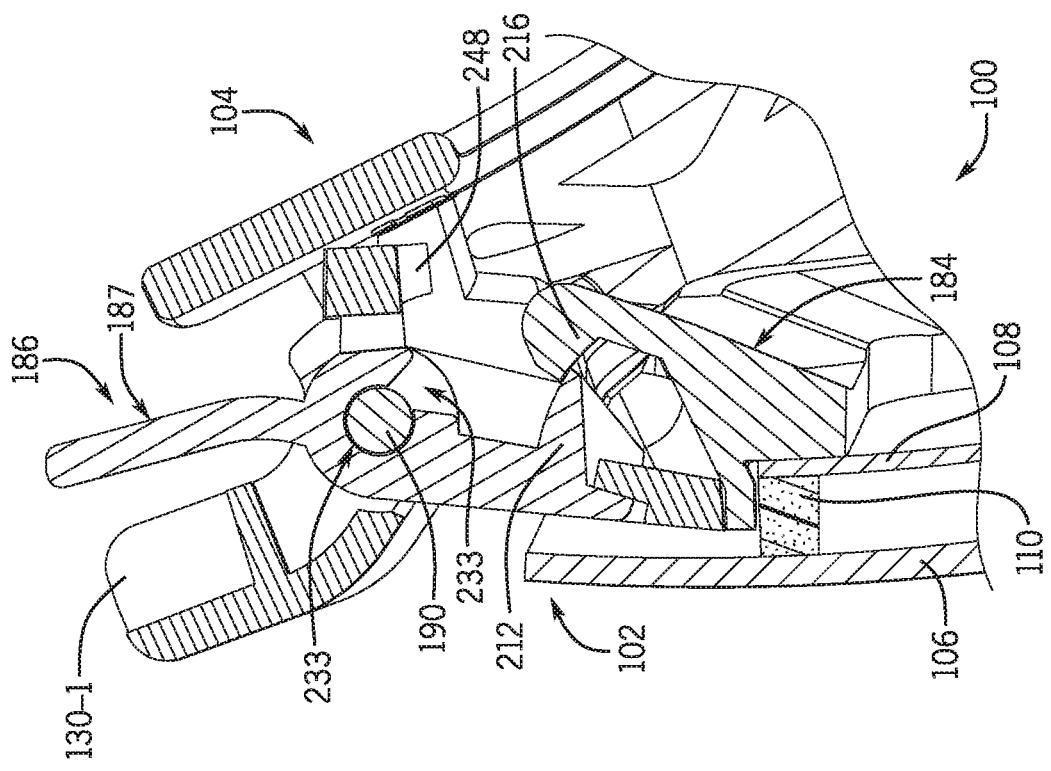
FIG. 11 is a detail view of the area circumscribed by detail line 11-11 in FIG. 10, illustrating a latch of the goggle of FIG. 1.

With continued reference to FIG. 10, the second latch component 186 of each latch 180-1, 180-2 may be movably coupled to the goggle frame 104. For example, as illustrated in FIG. 10, the second latch component 186 of each latch 180-1, 180-2 may be pivotally coupled to the goggle frame 104. As illustrated in FIG. 11, the second latch component 186 may include a lever 187. The lever 187 may be pivoted about a fulcrum (e.g., post 190) and may include a latch feature at the end of the lever opposite the actuation (or user-engagement) end of the lever. The lever 187 may be configured to be provided between a latched and unlatched position such as by moving (e.g., pivoting) the lever relative to the goggle frame 104 from a latched position, in which the latch 180-1, 180-2 is configured to retain the lens assembly 102 to the goggle frame 104, to an unlatched position, in which the lens assembly 102 may be removed from the goggle frame 104. In some embodiments, the second latch components 186 of each latch 180-1, 180-2 may be pivotally coupled to the goggle frame 104 using a common pivot axis for the outriggers 130-1, 130-2, thereby providing a more compact design. As illustrated in FIGS. 11 and 13, the second latch components 186 and the outriggers 130-1, 130-2 may pivot about a common post 190.

As described, each retention feature 180-1, 180-2 may include a latch component 186 (e.g., lever 187) and a tab 183 coupled to respective ones of the lens assembly 102 and the goggle frame 104. In the illustrated embodiment, the lever 187 is pivotally coupled to the goggle frame 104 and the tab 183 is fixedly coupled to the lens assembly 102 to allow the lever 187 to pivot away from the tab 183 while sliding the tab 183 past the lever during coupling and decoupling of the lens assembly 102 to the goggle frame 104. In other embodiments, the position of the lever 187 and the tab 183 may be reversed, for example the lever 187 may be pivotally coupled to the lens assembly 102 and the tab 183 may be coupled to the goggle frame 104.

The goggle frame 104 may include one or more features that restrict movement of the lever 187 in one or more directions. For example, the goggle frame 104 may be configured to restrict translational movement of the lever 187 such that the lever 187 is restricted to pivotal motion. As previously discussed, the lever 187 may be pivoted about the post 190, which restricts movement of the lever 187 lateral to the post 190. Referring to FIG. 13, the goggle frame 104 may include one or more walls that restrict axial movement of the lever 187. The one or more walls may include a lower wall 192, which may restrict downward movement of the lever 187 (e.g., movement toward the lower peripheral edge of the lens assembly 102), and an upper wall 194, which may restrict upward movement of the lever 187 (e.g., movement toward the upper peripheral edge of the lens assembly 102). As such, the lower and upper walls 192, 194 of the goggle frame 104 may restrict movement of the lever 187 axially along the post 190. As illustrated in FIG. 13, a fulcrum portion 232 of the lever 187 may fit between the lower and upper walls 192, 194 and may receive the post 190 via an aperture 231. The outriggers 130-1, 130-2 may extend beneath the lower wall 192 and above the upper wall 194 and may receive the post 190 therein, such that levers 187 and outriggers 130-1, 130-2 pivot about the same posts 190. In some embodiments, the goggle frame 104 may include a vertical wall 196, which may restrict pivotal movement of the lever 187 (e.g., pivotal movement about the post 190).

In some embodiments, the latch component 186 may be configured such that it returns to its closed or latched position after the lens assembly 102 has been attached or detached from the goggle frame 104. For example, the lever 187 may be biased toward its latched position. Referring to FIG. 13, when the lever 187 is pivoted toward an unlatched position, one or more arms 200 of the lever 187 may abut against the vertical wall 196 of the goggle frame 104 such that continued pivotal motion of the lever 187 resiliently deforms the one or more arms 200 and creates a preload in the one or more arms 200 that biases the lever 187 toward its latched position. By maintaining a preload in the one or more arms, the lever 187 is able to automatically snap back to the latched position without the application of user force. Although the one or more arms 200 are shown as extending substantially perpendicular to a length of the lever 187 (e.g., vertically) of the latch component 186, in some embodiments, such as the one shown in FIGS. 19A and 19B, the one or more arms 200 may extend in a direction parallel to or substantially parallel to the length of the lever 187 (e.g., horizontally). The embodiment shown in FIGS. 19A and 19B may provide a more vertically compact design whereas the embodiment shown in FIG. 13 may provide a more horizontally compact design. In other embodiments, the biasing feature may be implemented in a different manner, for example by spring loading the lever 187, by using magnetic force, or using a different combination of structural elements to restrain pivotal movement of the lever 187.

Each latch 180-1, 180-2 may be configured to cause the lever 187 to temporarily move (e.g., pivot) away from the tab 183 during attachment of the lens assembly 102 to the goggle frame 104. For example, the lever 187 and/or the tab 183 may include ramp features which may cooperate to cause the lever 187 of each latch 180 to move from its latched position to its unlatched position as the lens assembly 102 is advanced toward the goggle frame 104, e.g., without the application of user force to the lever 187 other than the force applied to advance the lens assembly 102 toward the goggle frame 104.

In some embodiments, the inner surface of the lever 187 may taper outwardly towards a forward end of the lever 187 defining a ramp 204 (see FIG. 13). The ramp 204 may be inclined such that the thickness of the lever 187 increases from the forward end of the lever 187 toward its pivot axis. The ramp 204 may cooperate with a ramp 208 on the tab 183 to facilitate automatic movement of the lever 187 from a latched position to an unlatched position during coupling of the lens assembly 102 to the goggle frame 104. The ramps 204, 208 may bear against each other as the lens assembly 102 is advanced toward the goggle frame 104 to cause the lever 187 to pivot out of its latched position against a force that biases the lever 187 towards its latched position.

The ramp 208 on the tab 183 may be defined on a side of the tab 183 (e.g., an outward-facing side) which faces the ramp 204 when the lens assembly 102 is positioned for coupling to the goggle frame 104. The ramp 208 may guide the ramp 204 on the lever 187 as the lens assembly 102, and thus the tab 183, is moved toward the goggle frame 104 to temporarily urge the lever 187 away from the tab 183. The ramp 208 may be inclined such that the lever 187 continues to pivot away from its latched position until the lens assembly 102 is magnetically coupled with the goggle frame 104, at which point the ramp 208 may pass by the ramp 204 such that the biased lever 187 is automatically pivoted back to its latched position to restrict inadvertent decoupling of the lens assembly 102 from the goggle frame 104. When the lever 187 is in the latched position, a ledge 212 on the lever 187 may be positioned behind a shoulder 216 on the tab 183 (see FIGS. 10 and 11) to inhibit removal of the tab 183 from the lever 187, and thus the lens assembly 102 from the goggle frame 104, until the lever 187 is pivoted from its latched position to its unlatched position by a wearer of the goggle 100.

Figure 12:
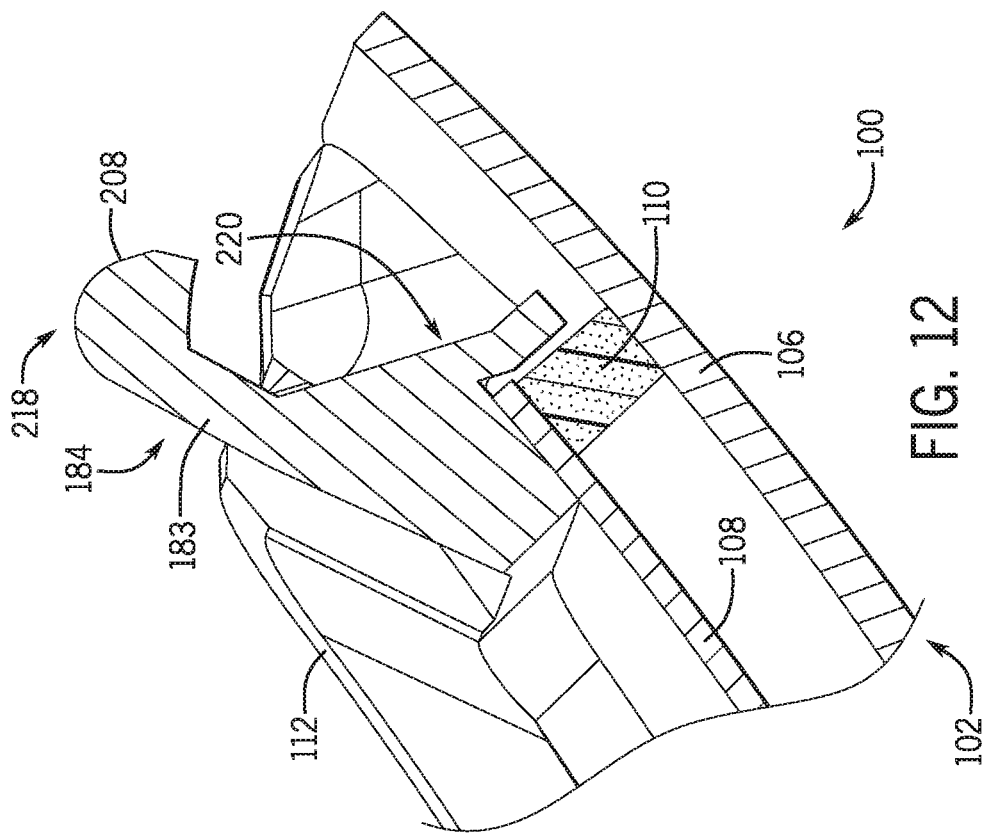
FIG. 12 is a detail view of the area circumscribed by detail line 12-12 in FIG. 10, illustrating a latch component of a lens assembly of the goggle of FIG. 1.

The tab 183 may be a generally plate-like structure with a barbed rearward end 218 as in the illustrated embodiment in FIG. 12. The tab 183 may be angled or rounded at its rearward end 218 (e.g., having a generally semi-circular or semi-ovular shape at its rearward end) to define the ramp 208. Although the tab 183 is described generally as plate like, this does not imply that the tab 183 is necessarily of constant thickness. While the tab 183 may have a constant thickness in some embodiments, in other embodiments, the tab's forward end 220 may include varying thickness along its length, as illustrated in FIG. 12 in which the forward end 220 of the tab 183 increases in thickness near its attachment to the lens frame 112. Also, it will be understood that the tab 183 need not have a perimeter that defines a regular shape. The perimeter of the tab 183 may define any irregular shape as may be suitable for a particular application. The tab 183 may be differently shaped in other embodiments than the examples specifically illustrated or described.

Figure 19A:
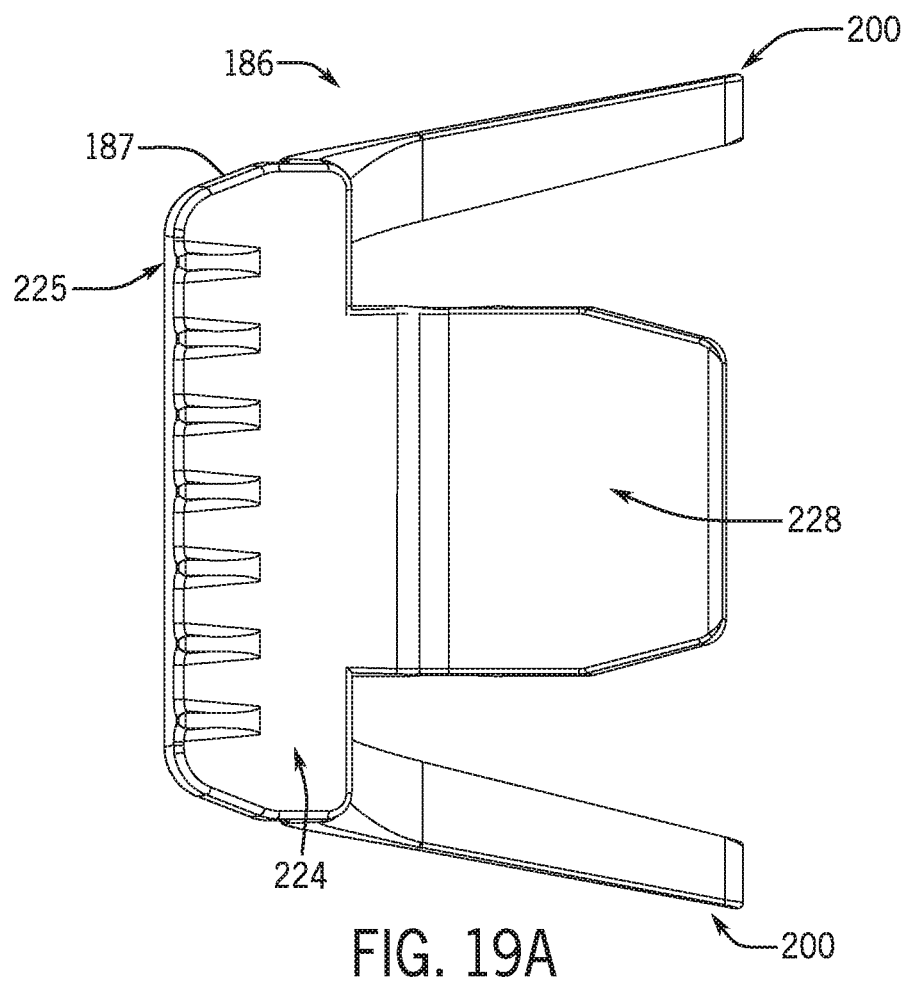
FIG. 19A is a view of a latch component according to another example of the disclosure.

The latch component 186 (e.g., lever 187) may include a user-engagement portion 224 and a latch portion 228 as in the illustrated embodiment in FIG. 13. The user-engagement portion 224 may be a generally plate-like structure configured for a wearer to press against to actuate the latch component 186 (e.g., move the lever 187 from its latched position to its unlatched position to enable removal of the lens assembly 102 from the goggle frame 104). The latch portion 228 may be angled or rounded at its forward end to define the ramp 204. The user-engagement portion 224 may be separated from the latch portion 228 by the fulcrum portion 232, which may define the aperture 231 for receiving the pivot pin or post 190. In some embodiments, as can be seen in FIG. 11, the aperture 231 may not fully enclose post 190 and include a gap 233. The fulcrum portion 232 may be formed of a resilient material and gap 233 may be sized such that the fulcrum portion 232 may be snap fit onto post 190. This may provide for easier assembly of the goggle frame 104. Although the user-engagement portion 224 is described generally as plate like, this does not imply that the user-engagement portion 224 is necessarily of constant thickness. The lever 186 may be differently shaped in other embodiments than the examples specifically illustrated or described. In some embodiments, such as the one shown in FIG. 19A, the user-engagement portion 224 may include a grip feature 225. In some embodiments, the grip feature 225 may be a raised pattern as shown in FIG. 19A. In other embodiments, the grip feature 225 may be implemented as one or more depressions in the user-engagement portion 224. The grip feature 225 may improve a user's grip on the user-engagement portion 224.

Figure 7:
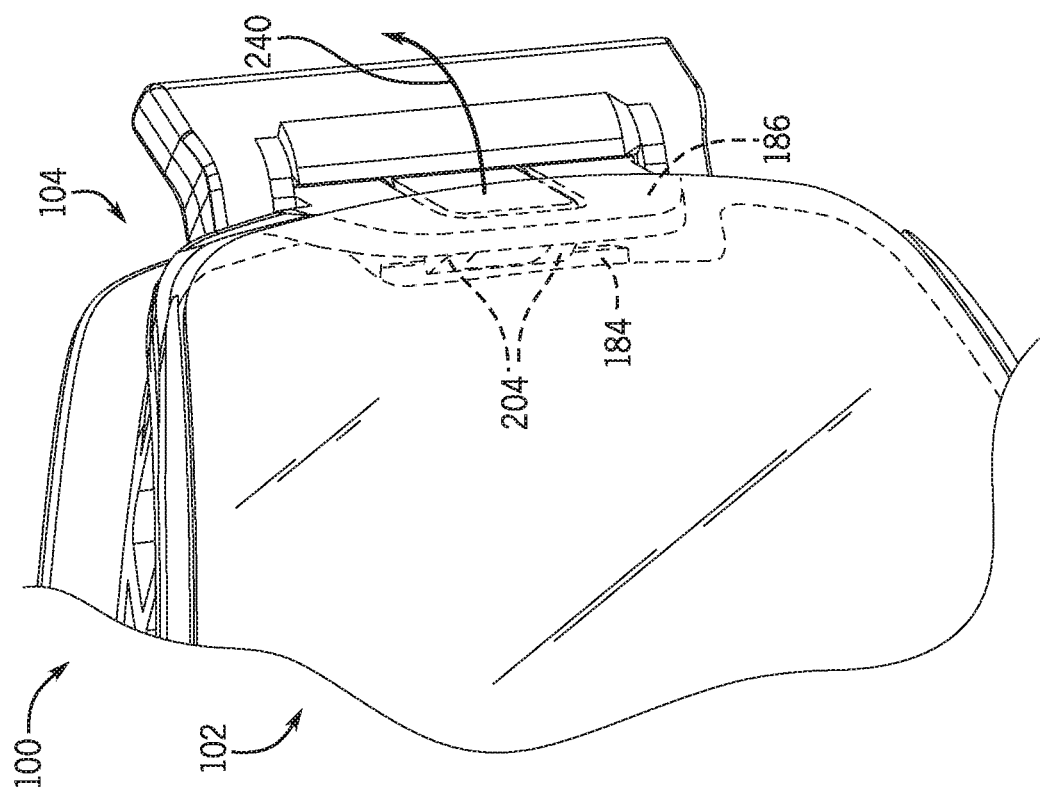
FIG. 7 is a partial front view of the goggle of FIG. 6 with the lens assembly being coupled to the goggle frame and illustrating movement of a latch component on the goggle frame when coupling the lens assembly to the goggle frame.
Figure 6:
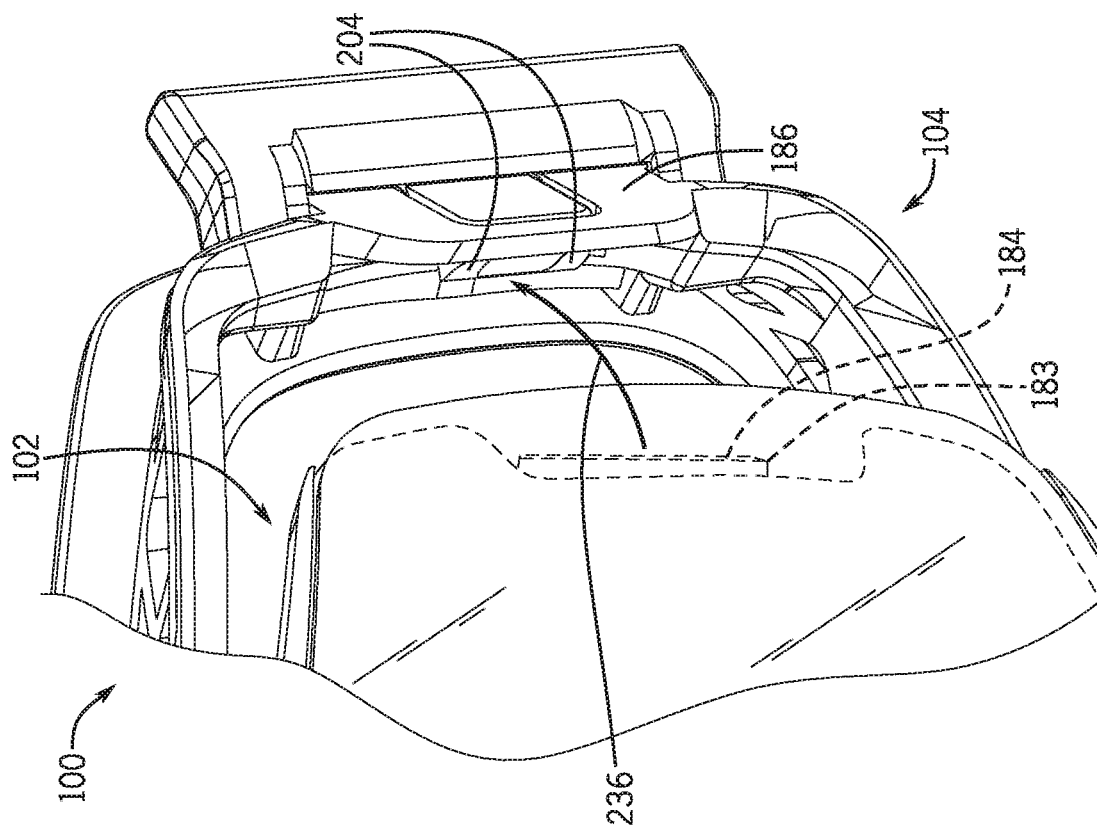
FIG. 6 is a partial front view of the goggle of FIG. 1 with a right side of a lens assembly spaced from a goggle frame and illustrating movement of the lens assembly when coupling the lens assembly to the goggle frame.

With reference to FIGS. 6-9, sequences for coupling and decoupling the lens assembly 102 to the goggle frame 104 in accordance with some examples are described in further detail below. FIGS. 6 and 7 show a sequence for attaching the lens assembly 102 to the goggle frame 104. As shown in FIG. 6, the lens assembly 102 is moved towards the goggle frame 104 (see direction arrow 236). As the lens assembly 102 advances toward the goggle frame 104, the tab 183 moves towards the lever 187. When the lens assembly 102 is positioned sufficiently close to the lever 187, the tab 183 may engage the lever 187, for example by engaging its ramp 208 (see FIG. 12) with the ramp 204 defined on the lever 187. As described, the tab 183 and the lever 187 may be configured to allow the tab 183 to slide along the ramp 204 of the lever 187. As the lens assembly 102 advances further toward the goggle frame 104, e.g., as shown in FIG. 7, the tab 183 may pivot the lever 187 toward an unlatched position, as shown by arrow 240 in FIG. 7. By automatically, it is generally implied that the pivoting of the lever 187 from its latched position to its unlatched position occurs without the application of user force pivot the lever 187 but rather as the result of the cooperation of components of the latch (e.g., the cooperation of the tab 183 and the lever 187).

As the user continues to move the lens assembly 102 towards the goggle frame 104, the ramp 208 on the tab 183 (see FIG. 12) passes over the ramp 204 on the lever 187. Once the ramp 204 of the lever 187 has cleared the ramp 208 on the tab 183, the lever 187 automatically pivots (opposite the direction of arrow 240 in FIG. 7) into its latched position, as shown in FIG. 8. In this position, the lens assembly 102 is not removable from the goggle frame 104 unless a user actuates one of the latches 170-1, 170-2. The return of the lever 187 from the unlatched position to the latched position is automatic (e.g., responsive to the biasing force, which acts in the direction opposite arrow 240 in FIG. 7) and without further application of user force. In this manner, a latching mechanism as described herein may enable the near effortless coupling of the lens assembly 102 to the goggle frame 104, e.g., without requiring the user to perform a complex sequence of opening and closing the latches 170-1, 170-2. All the user may be required to do is move the lens assembly 102 close to the goggle frame 104, and the magnetic materials of the lens assembly 102 and the goggle frame 104 cooperate with one another to magnetically couple the lens assembly 102 to the goggle frame 104, which movement causes the lever 187 to open and close, thereby securing the lens assembly 102 to the goggle frame 104. As the lever 187 returns to the latched position, the extensions 162 and recesses 160 (see FIGS. 2-5) may facilitate the proper alignment and positioning of the lens assembly 102 to the goggle frame 104.

To detach the lens assembly 102 from the goggle frame 104, the user applies a force on one of the levers 187 as shown by arrow 176 in FIG. 9 to pivot the lever 187 about the post 190 (see e.g., FIG. 11) away from the tab 183, allowing the tab 183 to slide out of the goggle frame 104 in the direction generally opposite the direction of insertion to remove the respective end of the lens assembly 102 from the goggle frame 104. The outriggers 130-1, 130-2 may be prevented from inadvertently actuating the levers 187, thereby inhibiting inadvertent detachment of the lens assembly 102 from the goggle frame 104. For example, as illustrated in FIG. 11, each outrigger (e.g., outrigger 130-1 illustrated in FIG. 11) may engage a stop 248 formed on the goggle frame 104 that prevents the outriggers (see outrigger 130-1 in FIG. 11) from pivotal movement towards the lever 187, thereby inhibiting the outriggers 130-1, 130-2 from actuating the levers 187.

As previously described, the biasing feature may enable the automatic return of the lever 187 to its latched position once the lever 187 has cleared the distal end of the tab 183. After one of the ends of the lens assembly 102 is detached from the goggle frame (see FIG. 9), the wearer may grasp the free end 250 of the lens assembly 102 and move the lens assembly 102 in a lateral direction (see arrow 254 in FIG. 9) away from the engaged latch 170-1 to remove the lens assembly 102 from the goggle frame 104. As illustrated in FIGS. 10 and 11, moving the lens assembly 102 in the lateral direction (see arrow 254 in FIG. 9) allows removal of the tab 183 from behind the lever 187 without actuating the lever 187. In this manner, the lens assembly 102 may be detached from the goggle frame 104 by actuation of only one of the latches 170-1, 170-2. In other words, the wearer may manually actuate one of the latches 170-1, 170-2 on one side of the goggle 100, pivot the lens assembly 102 about the other, non-actuated latch 170-1, 170-2 on the other side of the goggle 100 until the other latch disengages itself naturally without having to actuate the latch. To naturally disengage the other latch, the lens assembly 102 may be pivoted until all of the extensions 162 are removed from the recesses 160 (see FIGS. 2-5) and then may be laterally removed from the goggle frame 104. In some embodiments, the lens assembly 102 is pivoted about twenty to thirty degrees to naturally disengage the other latch. The pivotal range may vary depending on the specific goggle application.

As can be seen in FIGS. 10 and 11, when lens assembly 102 is coupled to goggle frame 104, at least a portion of the latch component 186 is positioned between the outer lens 106 and tab 183. The latch component 186 may be arranged such as to reduce the risk of contact with the lens, e.g., by limiting the rotation of the lever 187. In some embodiments, contact between the latch component 186 and outer lens 106 may be avoided by arranging the tab 183 such that it extends sufficiently laterally outward from the outer lens 106 thereby positioning the latch component 186 in a manner in which its actuation does not risk it contacting the lens. In some embodiments, providing at least a portion of the latch component 186 between the outer lens 106 and tab 183 may reduce the risk of lever 187 being in advertently actuated by an object near the edge of the goggle 100 (e.g., catching on a wearer's hood or helmet strap). Providing at least a portion of latch component 186 between the outer lens 106 and tab 183 may serve an aesthetic purpose of at least partially obscuring the latch component 186 from view. As can be seen in FIGS. 11 and 12, the tab 183 may be coupled to the lens assembly 102 such that tab 183 does not contact outer lens 106.

As described, the user engagement portion of the lever 187 may pivot outward in a direction away from the lens assembly 102 during coupling of the lens assembly 102 to the goggle frame 104. In other embodiments, this functionality may be reversed, with the user engagement portion of the lever 187 pivoting inward in a direction towards the lens assembly during coupling of the lens assembly 102 to the goggle frame 104. As will be appreciated, the combination of components described herein may facilitate a virtually effortless attachment and detachment of the lens assembly 102 to the goggle frame 104, which may provide a better user experience. The near effortless engagement of the lens assembly 102 to the goggle frame 104 in accordance with the present disclosure may enable the user to install and remove the lens assembly 102 without touching the lens surface (that is by only handling the lens assembly 102 by its edges), which may address some shortcomings of existing interchangeable goggle designs.

The lens assembly 102 may include multiple user engagement features located around a periphery of the lens (e.g., outer lens 106 and/or inner lens 108) for a wearer to grasp during coupling or decoupling of the lens assembly 102 to or from, respectively, the goggle frame 104, thus avoiding touching the lens. For example, as illustrated in FIGS. 1-4 and 14, the lens assembly 102 may include multiple rim portions 256 located around a periphery of the outer lens 106. The rim portions 256 may protrude outwardly from the outer lens 106 such that the rim portions 256 form a semi-rimless frame around the periphery of the outer lens 106 for a wearer to grasp during coupling or decoupling of the lens assembly 102 to or from, respectively, the goggle frame 104. The rim portions 256 may be located near the corners of the lens assembly 102 to facilitate handling of the lens assembly 102 by the wearer. For example, as illustrated in FIG. 4, a first rim portion 256-1 and a fourth rim portion 256-4 may be located at opposing corners of one end- or side-portion of the lens assembly 102, and a second rim portion 256-2 and a third rim portion 256-3 may be located at opposing corners of the other end- or side-portion of the lens assembly 102. During use, the wearer may grasp the first and fourth rim portions 256-1, 256-4 and/or the second and third rim portions 256-2, 256-3 to manipulate the lens assembly 102, such as to pivot one end of the lens assembly 102 away from the goggle frame 104 during removal of the lens assembly 102 from the goggle frame 104. The rim portions 256 may be formed on the lens frame 112 (see FIG. 14) and may protrude outwardly and forwardly from the lens frame 112 such that the rim portions 256 extend over a perimeter edge of the outer lens 106, thereby ensuring the wearer does not inadvertently touch the outer lens 106 while grasping the tabs 256. Although the lens assembly 102 illustrated in FIGS. 1-4 and 14 includes four rim portions 256-1, 256-2, 256-3, 256-4 (generally referred to as rim portions 256), the lens assembly 102 may include more or less than four rim portions. The lengths of the rim portions 256 along the periphery of the outer lens 106 may be longer or shorter than the rim portions 256 in the example shown in FIGS. 1-4.

Figure 16:
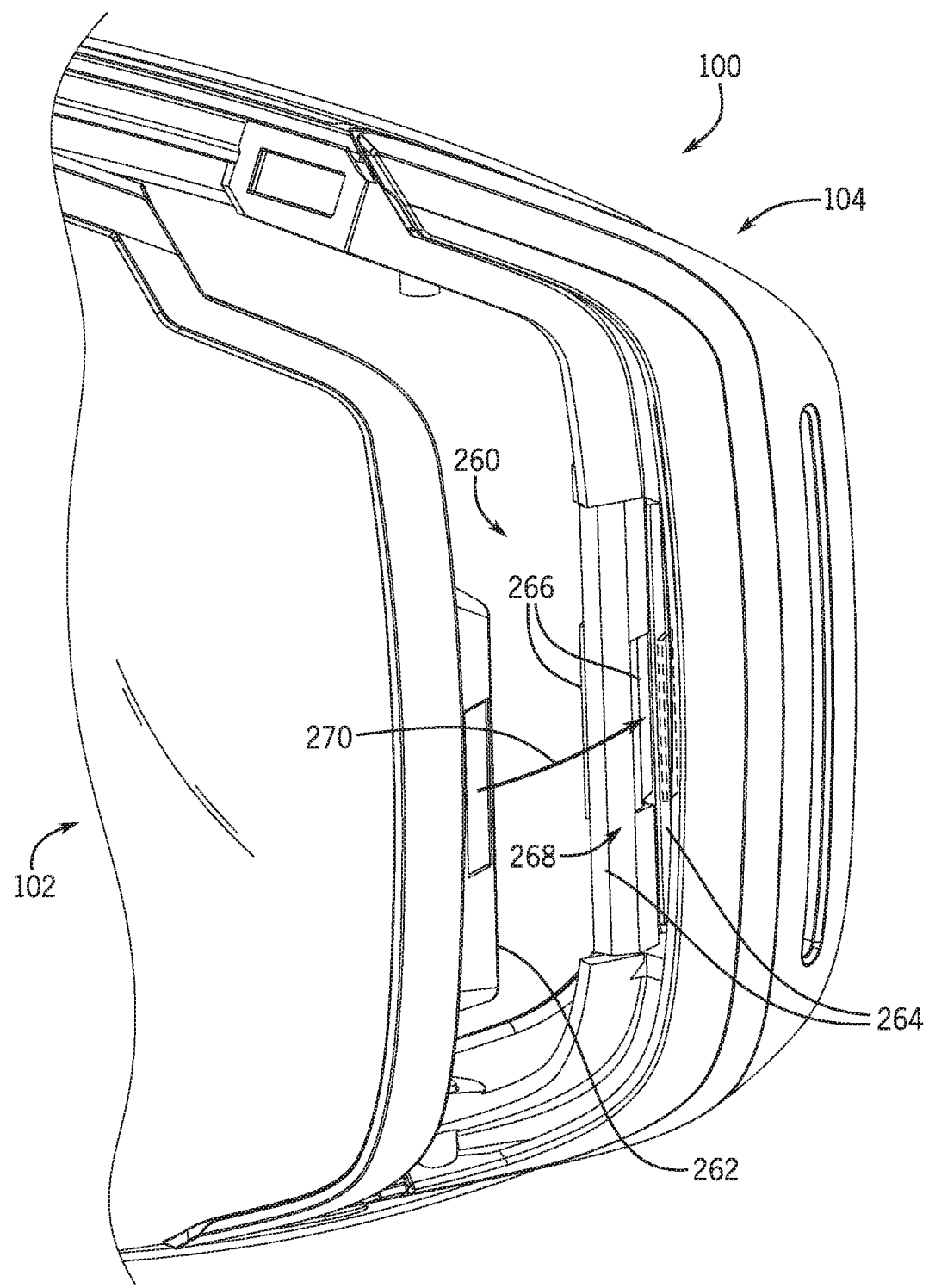
FIG. 16 is a partial front view of the goggle of FIG. 1 with a right side of a lens assembly spaced from a goggle frame and illustrating movement of the lens assembly when coupling the lens assembly to the goggle frame in accordance with an alternative latch mechanism of the present disclosure.

FIGS. 16-18 illustrate a retention feature 260 in accordance with further embodiments of the present disclosure. The retention feature 260 may include a first latch component (e.g., a gate 262) and a second latch component (e.g., strips 264). The gate 262 may include (e.g., be formed at least partially of) a magnetic material (e.g., a permanent magnet such as a rare earth magnet, or ferromagnetic material such as iron or steel). Each strip 264 may include a magnet 266 (e.g., a magnetic material such as iron or a neodymium or other type of permanent magnet) affixed thereto, forming magnetic strips 264. Each magnet 266 may have the same polarity as each other such that the magnets 266 are configured to repel each other to maintain the strips 264 in a spaced-apart relationship defining a gap 268 therebetween. When the gate 262 is inserted between the strips 264 during coupling of the lens assembly 102 to the goggle frame 104 (see direction arrow 270 in FIGS. 16 and 17), the gate 262 blocks the repelling force of the strips 264, and the magnetic strips 264 are magnetically attracted to the gate 262 (see FIG. 18) to secure the lens assembly 102 to the goggle frame 104. In some embodiments, the second latch component may include a first magnetic strip 264 and the second magnetic strip 264 is built into goggle frame 104.

Figure 20:
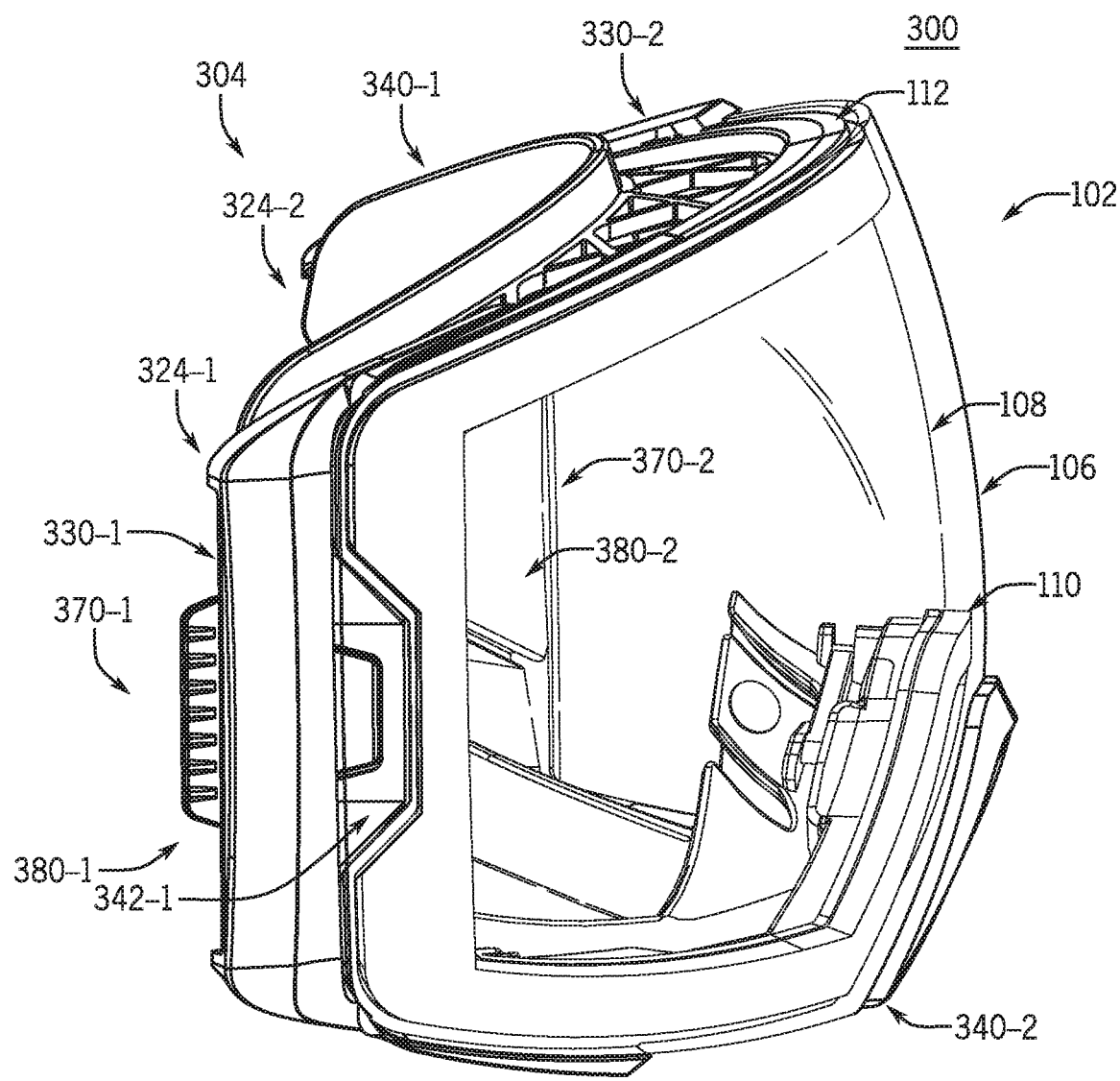
FIG. 20 is an isometric view goggle according to another example of the disclosure.

FIGS. 20-25 illustrate a goggle 300 in accordance with the principles of the present disclosure. As seen in FIG. 20, goggle 300 may include goggle frame 304, which may be coupled to lens assembly 102 to form goggle 300. As will be described further below, goggle frame 304 may couple to lens assembly 102 in a similar manner as goggle frame 104. Goggle 300 may include first and second opposite end portions 324-1 and 324-2. First and second outriggers 330-1 and 330-2 may be fixedly or pivotally coupled to the goggle frame 304 to provide an attachment mechanism for a strap (not shown in FIG. 20), such as strap 128 in FIG. 1.

Figure 21:
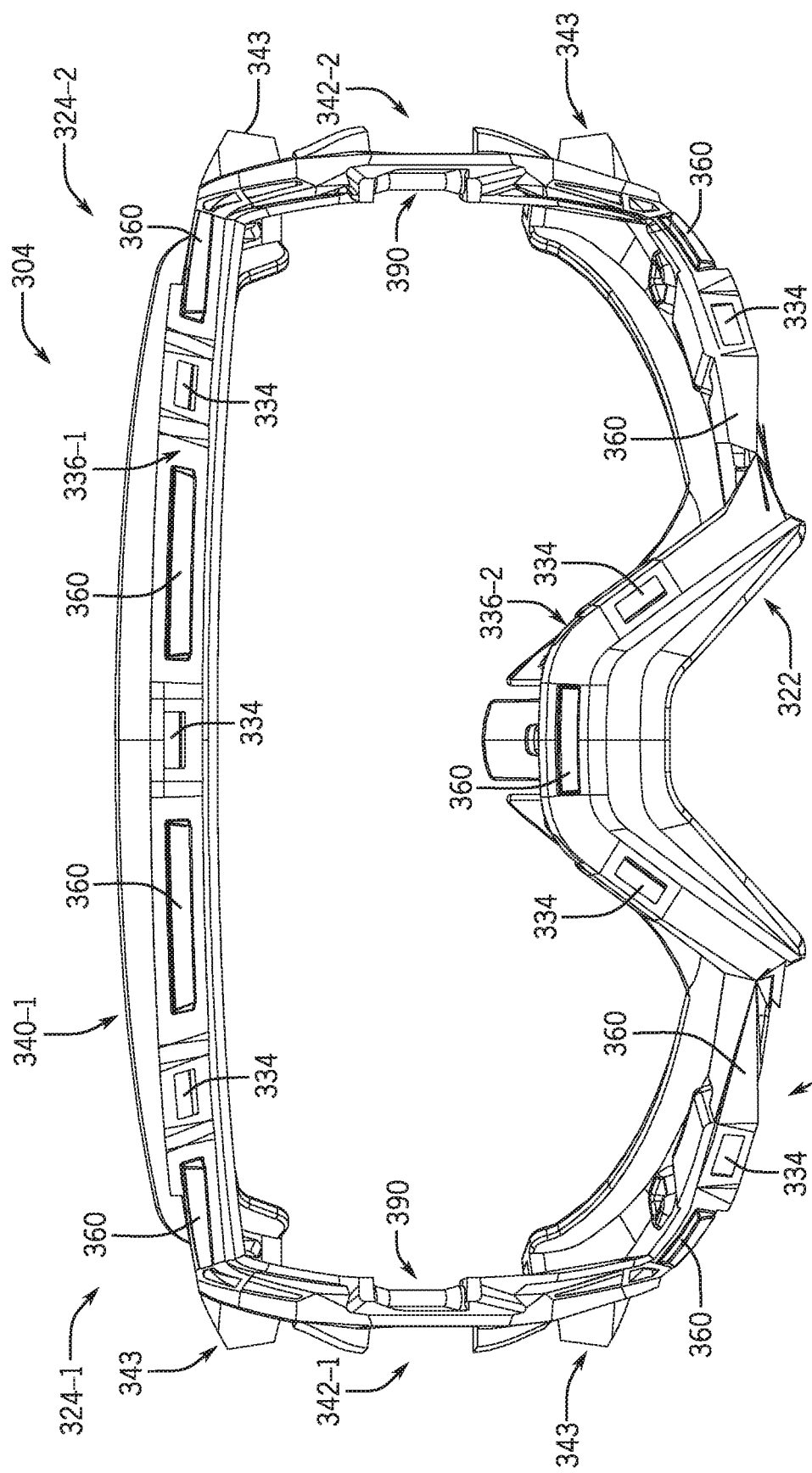
FIG. 21 is a front view of a portion of a goggle frame of the goggle shown in FIG. 20.

The goggle frame 304 in the example in FIG. 21 includes a face gasket, which in this example is provided by two partial frame rings, specifically upper frame ring 340-1 and lower frame ring 340-2. The goggle frame 304 also include an interface component, which is provided by two side portions, specifically the first and second side portions 342-1 and 342-2, respectively. The partial frame rings 340-1 and 340-2 and side portions 342-1 and 342-2 may reduce the weight of the goggle frame 304 compared to goggle frame 104. Additionally, different size goggle frames may be more easily manufactured (without needing differently sized molds for the frame ring) by using different length side portions with the same upper and lower frame rings, which can improve the manufacturability of the goggle. The partial frame rings 340-1 and 340-2 may be formed of a relatively soft material (e.g., a thermoplastic elastomer such as TPU), which may allow the partial frame rings 340-1 and 340-2 to more closely and comfortably conform to a user's face. The side portions 342-1 and 342-2 may be formed of a harder or more rigid material (e.g., a rigid plastic such as nylon), thereby providing a stable base or interface for coupling the removable lens assembly 102 to the goggle frame 304.

In some embodiments, side portions 342-1 and 342-2 may be coupled to upper frame ring 340-1 and lower frame ring 340-2 by an overmolding process. In an example manufacturing process, the side portions 342-1 and 342-2 are formed (e.g., by injection molding, compression molding or other suitable molding process or via an additive manufacturing process such as stereolithography (SLA) or other 3D printing process). After the side portions are formed into the suitable rigid plastic material (e.g., cured nylon, resin or another), the side portions are inserted into a mold tool where they are overmolded with the thermoplastic elastomer (e.g., TPU) of the face gasket. As described further herein, the magnets may then be inserted into pockets of the frame gasket. In other examples, the magnets may be insert molded with the face gasket (i.e., the magnets are appropriately positioned in the mold tool before the addition of the thermoplastic elastomer such that they may affix to the face gasket during the curing process. In further examples (e.g., which can apply to the goggle embodiment in FIG. 13, the manufacturing sequence may involve forming the interface component (e.g., frame ring) first such by injection molding or other suitable process, then inserting the magnets into magnet seats in the interface components, and overmolding with the face gasket material to sandwich and thereby secure the magnets to the goggle frame. In yet other examples, the manufacturing sequence may not involve any overmolding. That is, the face gasket component(s) and the interface component(s) may be each separately formed via a suitable process such as molding or additive manufacturing and the two separately formed components may be attached to one another via an adhesive and/or mechanical coupling (e.g., fasteners, snap features, etc.)

Figure 22:
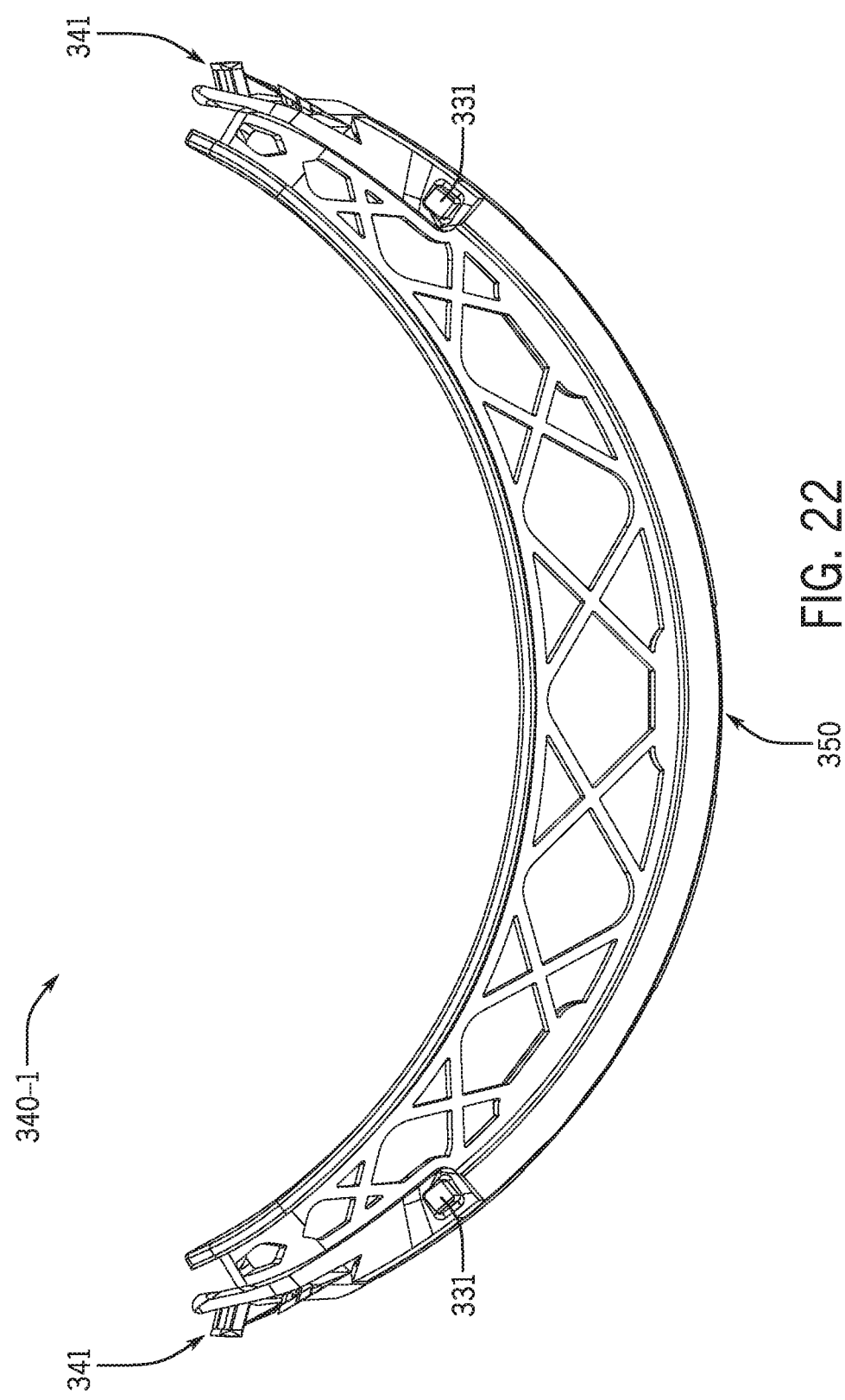
FIG. 22 is a top view of an upper portion of the goggle frame shown in FIG. 21.
Figure 23:
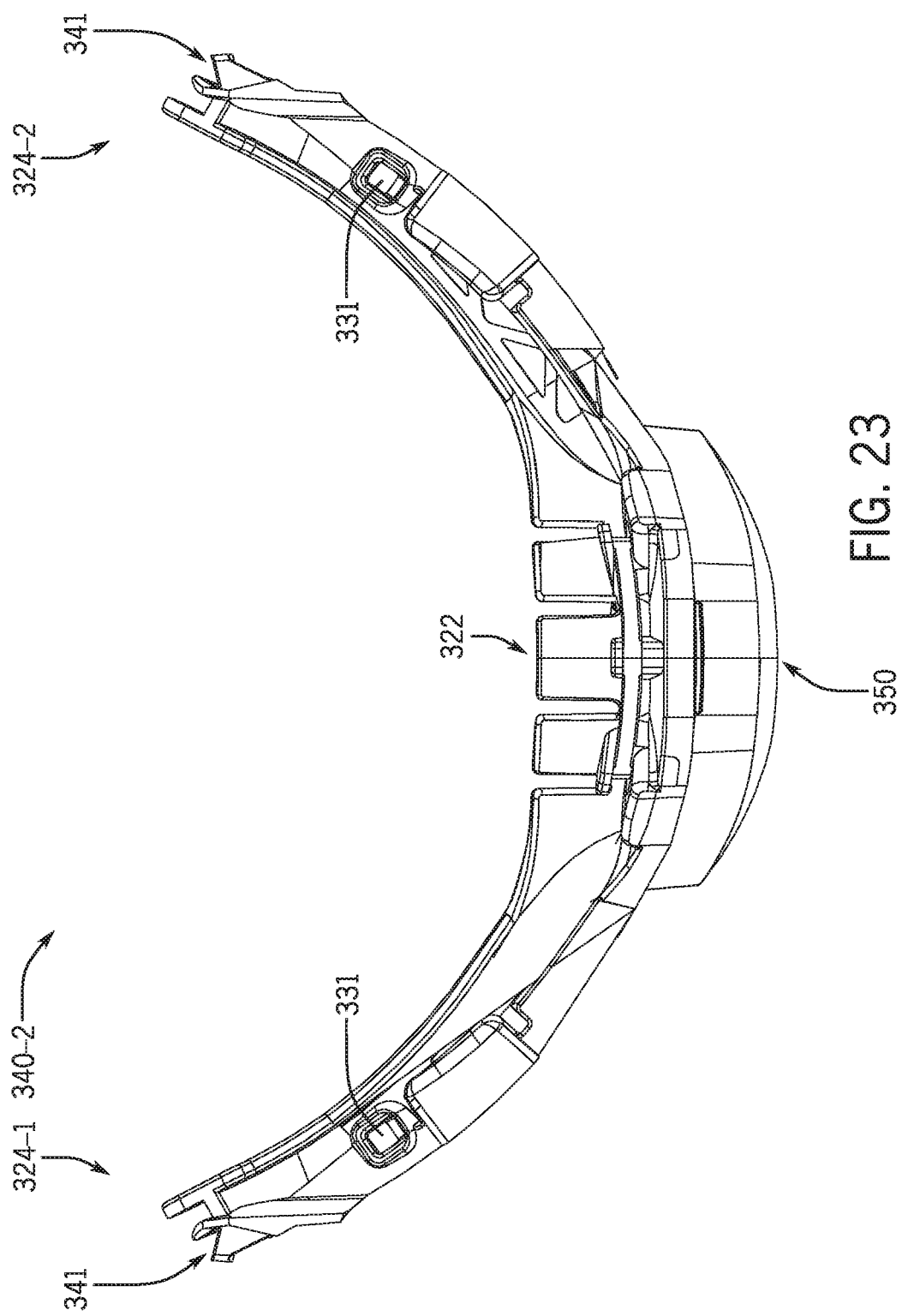
FIG. 23 is a top view of a lower portion of the goggle frame shown in FIG. 21.
Figure 24:
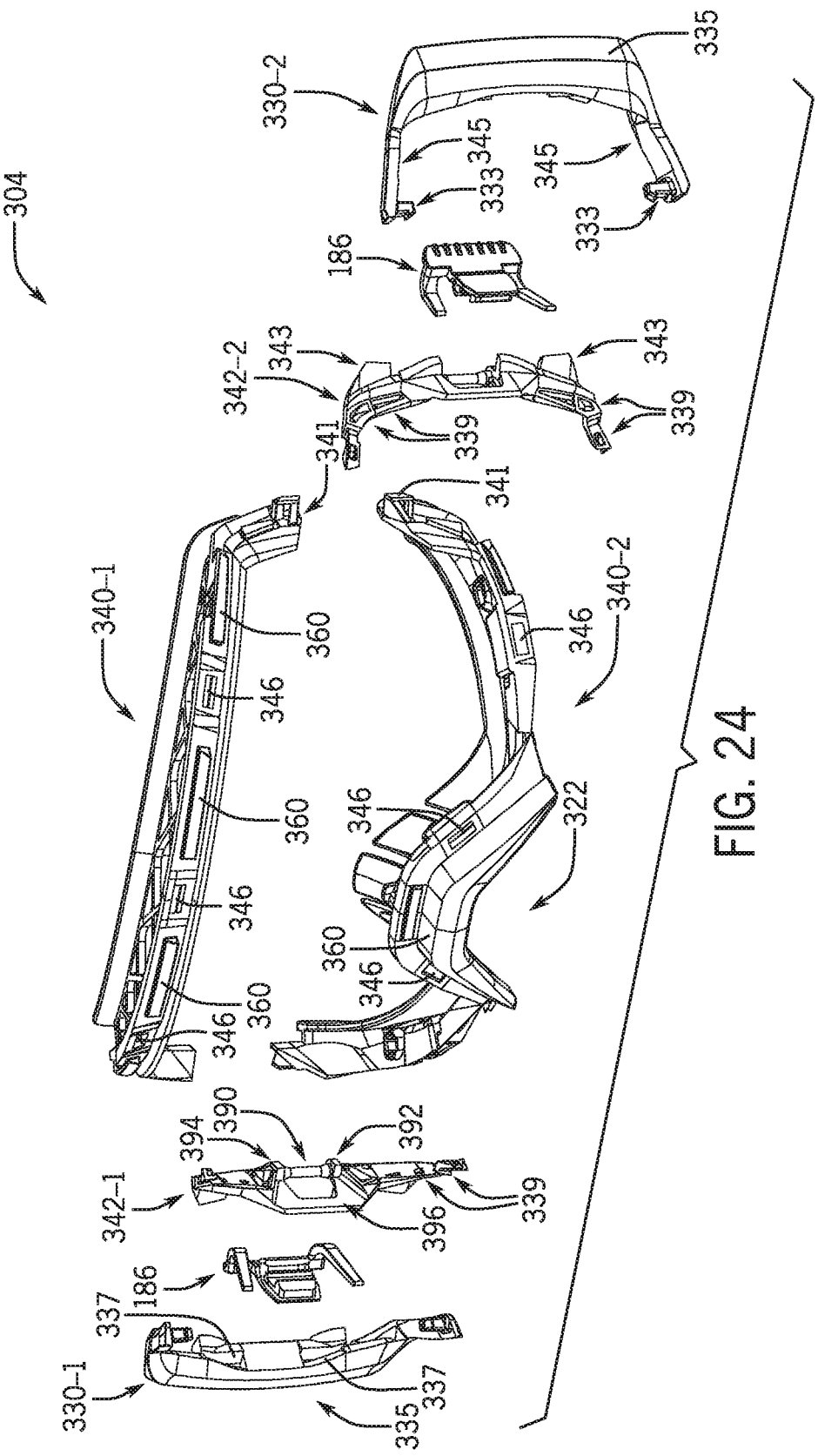
FIG. 24 is an exploded view of the goggle frame shown in FIG. 20.

Referring to FIGS. 22-24, the partial frame rings 340-1 and 340-2 may include one or more protrusions 341 at end portions 324-1 and 324-2 configured to engage cavities 339 formed in the side portions 342-1 and 342-2. In some embodiments, such as those shown in FIG. 22-24, the protrusions 341 may have a hook-like structure which may provide additional retention of the side portions 342-1 and 342-2 to the partial frame rings 340-1 and 340-2.

Referring to FIG. 21, lower frame ring 340-2 may include a nose pad 322 which may be configured to accommodate the nose of a wearer when the goggle 300 is worn. The nose pad 122 may be formed of the same material as the rest of the lower frame ring 340-2. In some embodiments, an additional material (not shown) may be coupled to a surface of nose pad 122 adjacent to the nose of the wearer when worn. The additional material may be a soft or flexible polymeric material (e.g., foam) which may further conform to the user's nose for a comfortable fit and provide additional cushioning.

Referring to FIGS. 22-24, upper frame ring 340-1 and lower frame ring 340-2 may include holes 331 near end portions 324-1 and 324-2 configured to receive prongs 333 of outriggers 330-1 and 330-2. The prongs 333 may retain outriggers 330-1 and 330-2 to the partial frame rings 340-1 and 340-2. In some embodiments, the prongs 333 may rotate within holes 331, pivotally coupling the outriggers 330-1 and 330-2 to the goggle frame 304. In other embodiments, the prongs 333 may be configured to engage holes 331 such that the outriggers 330-1 and 330-2 are fixedly attached to the partial frame rings 340-1 and 340-2.

Returning to FIG. 21, partial frame rings 340-1 and 340-2 may have angled surfaces 336-1 and 336-2. Angled surfaces 336-1 and 336-2 may be angled inward and rearward toward a center of the goggle frame 304 to facilitate alignment of the lens assembly 102 with the goggle frame 304. In some embodiments, the angled surfaces 336-1 and 336-2 may be oriented at a forty-five degree angle relative to a plane defined by the curvature of the outer lens 106 to facilitate alignment of the lens assembly 102 with the goggle frame 304. The angled surfaces 336-1 and 336-2 may define recesses 360. The recesses 360 may be positioned and shaped to correspond with extensions 162 of lens assembly 102. In other embodiments, the goggle frame 304 may include extensions and the lens assembly 102 may include recesses. The corresponding recesses and extensions may facilitate alignment between goggle frame 304 and lens assembly 102.

Referring to FIGS. 21 and 24, similar to goggle frame 104, goggle frame 304 may include magnetic materials (e.g., magnetic elements) for magnetic coupling with corresponding magnetic materials on the lens assembly 102. For example, partial frame rings 340-1 and 340-2 may include magnets 334 exposed along angled surfaces 336-1 and 336-2. The magnets 334 may be positioned to correspond to the positions of magnets 154 on lens assembly 102. The magnets 334 may have polarities opposite those of magnets 154 to facilitate coupling of lens assembly 102 and goggle frame 304. In some embodiments, the magnets 334 may have a trapezoidal shape surface. Pockets 346 may be defined in the upper and lower frame rings 340-1 and 34-2 along angled surfaces 336-1 and 336-2 between adjacent recesses 360. The pockets 346 may have a generally trapezoidal shape oriented such that the opening of the pockets 346 at the angled surfaces 336-1 and 336-2 are smaller than the bottoms of the pockets 346. The shape of the pockets 346 may correspond to the trapezoidal shape of the magnets 334 such that the magnets 334 are retained in the pockets 346 and exposed surfaces of the magnets 334 are flush with the angled surfaces 336-1 and 336-2. In some embodiments, the partial frame rings 340-1 and 340-2 may be temporarily deformed (e.g., bent) such that the opening to the pockets 346 are widened. The magnets 334 may be placed inside the pockets 346 during deformation and once the partial frame rings 340-1 and 340-2 are returned to their original shapes, the magnets 334 may be retained within the pockets 346. In some embodiments, an adhesive may be applied inside the pockets 346 to provide additional retention of the magnets 334 in the pockets 346. Although goggle frame 304 is shown including seven magnets 334 in FIG. 21, it is understood that goggle frame 304 may include more or fewer magnets 334 in other embodiments.

Similar to goggle frame 104, goggle frame 304 may include additional retention features to secure lens assembly 102 to the goggle frame 304. For example, as illustrated in FIG. 20, goggle frame 304 may include retention features 370-1 and 370-2 located at side portions 342-1 and 342-2. As illustrated in FIG. 20, the retention features 370-1 and 370-2 may be at least partially concealed by outriggers 330-1 and 330-2, respectively.

Figure 19B:
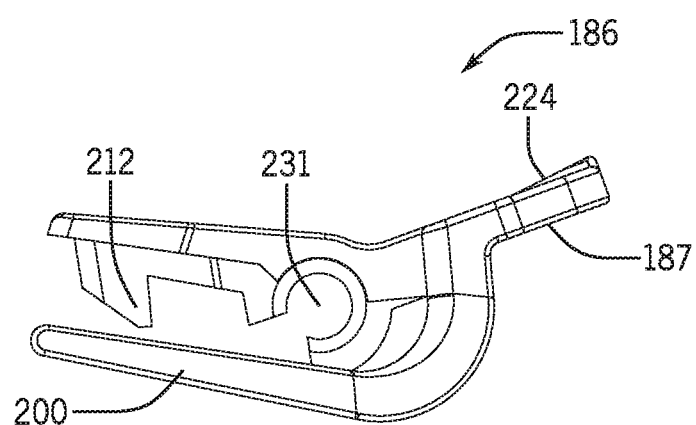
FIG. 19B is another view of the latch component shown in FIG. 19A.

In some embodiments, the retention features 370-1 and 370-2 may comprise latches. For example, as illustrated in FIG. 24, the goggle 300 may include a first latch 380-1 and second latch 380-2. The latches 380-1 and 380-2 may be coupled to or proximate the side portions 342-1 and 342-2, respectively. Each latch 380-1 and 380-2 may include a first latch component 184 coupled to the lens assembly 102. That is, portion of the latch included with the lens assembly 102 may be the same as the latch component 184 described in reference to FIGS. 3 and 10-12 in some embodiments (e.g., tab 183). Each latch 380-1 and 380-2 may further include a second latch component 186 coupled to the goggle frame 304. That is, the second latch component 186 may be the same as the latch component 186 shown in FIGS. 6-11 and 13 in some embodiments. In other embodiments, component 186 may be the same as the latch component 186 illustrated in FIGS. 19A and 19B. In the examples described in reference to FIGS. 20, 24 and 25, the latch component 186 of FIGS. 19A and 19B is shown.

Figure 25:
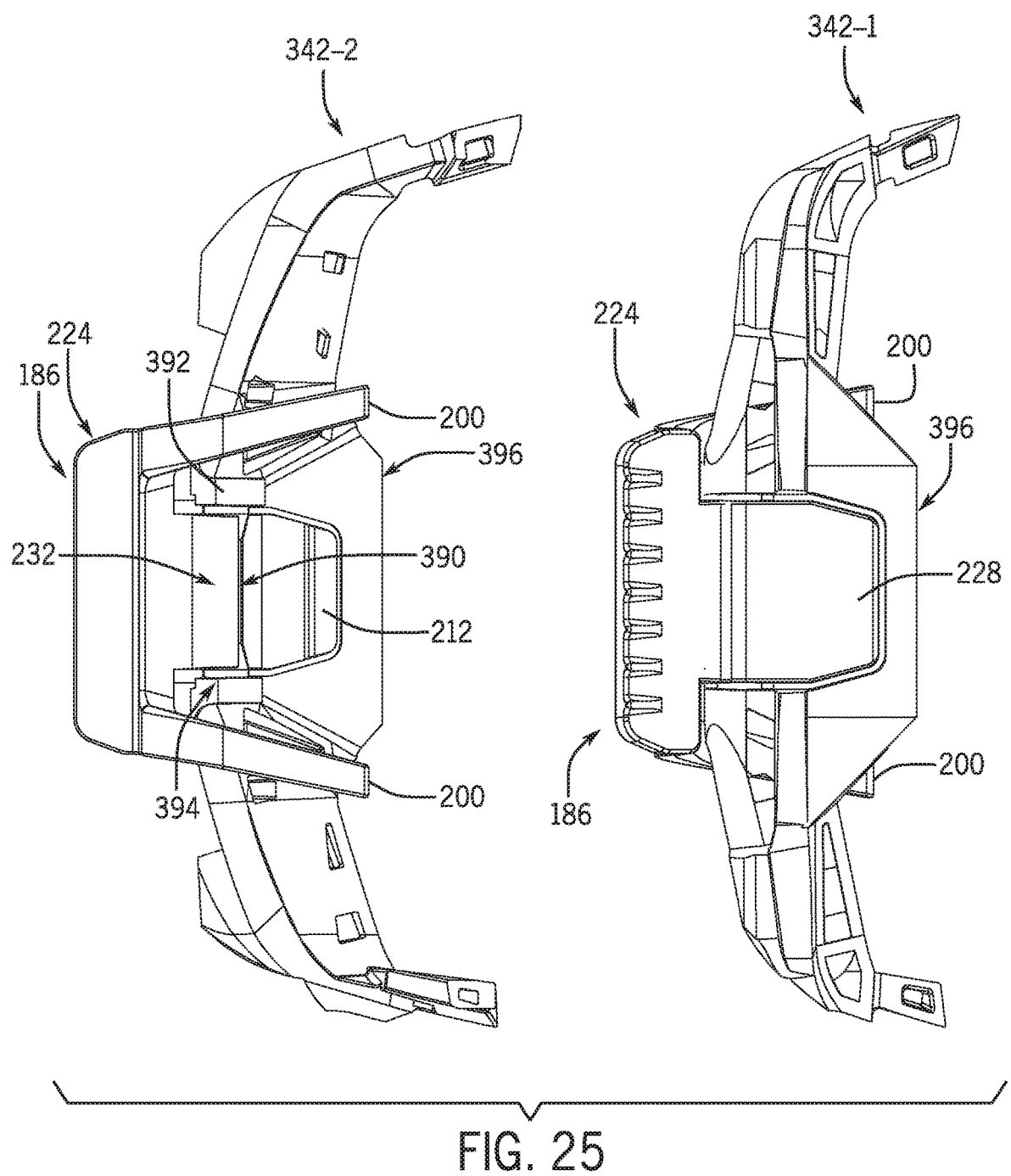
FIG. 25 is an isometric side view of side portions and latches of the goggle frame shown in FIG. 24.

With reference to FIGS. 24 and 25, the second latch component 186 of each latch 180-1 and 180-2 may be movably coupled to the goggle frame 104 at side portions 342-1 and 342-2, respectively. Side portions 342-1 and 342-2 may each include a post 390. For convenience, reference will be made only one of the side portions, but it should be understood that equivalent elements and arrangement of elements may be present on both side portions 342-1 and 342-2 in some embodiments. As shown in FIG. 25, the aperture 231 may be configured to receive post 390 pivotally coupling the latch component 186 to the side portion 342. The post 390 may restrict movement of the latch component 186 lateral to the post 390. The side portion 342 may include lower wall 392 and upper wall 394 on opposite ends of the post 390. The lower wall 392 and upper wall 394 may restrict the up and down movement of the latch component 186. In some embodiments, side portion 342 may include side wall 396 which may restrict pivotal movement of the latch component 186 and/or provide a base for arms 200 to apply a biasing force. In some embodiments, portions of the partial frame rings 340 may be adjacent to the side wall 396 of the side portion 342. In some embodiments, a portion of the arms 200 of the latch component 186 may apply a biasing force against the portions of the partial frame rings 340 adjacent to side wall 396.

Referring to FIGS. 21 and 24, side portion 342 may include stops 343. In some embodiments, such the embodiment illustrated in FIG. 21, stops 343 are in the form of flanges that angle outward from goggle frame 304. As shown in FIG. 24, the outrigger 330 may include recesses 337 having shapes corresponding to stops 343. The stops 343 may restrict pivotal movement of outrigger 330 to prevent the outrigger 330 from actuating latch component 186 when the outrigger 330 is pivotally attached. When the outrigger 330 is fixedly attached to the goggle frame 304, the stops 343 may space the outrigger 330 from the latch component 186 and restrict inadvertent rotation of the outrigger 330 due to impact or other forces on the goggle frame 304. This may prevent inadvertent disengagement of lens assembly 102 from goggle frame 304.

Unlike the embodiment of google frame 104, the outrigger 330 and latch component 186 do not share a common attachment point and/or pivotal axis in the embodiment of goggle frame 304. As shown in FIG. 24, the outrigger 330 includes a vertical panel 335 for coupling to a strap (not shown) with arms 345 extending from either end of the vertical panel 335. The arms may include the prongs 333 described previously that allow the outrigger to be fixedly or pivotally coupled to the partial frame rings 340. The pivotal axis of the latch component 186 is near an end portion 324 of the goggle 300, whereas the attachment point and/or pivotal axis of the outrigger 330 is closer to a central point 350 of the arc of the goggle 300 as shown in FIGS. 22-23. The separate pivotal axes may further reduce interference of the outrigger 330 with the latch component 186.

The process of coupling and decoupling goggle frame 304 and lens assembly 102 may be equivalent to the sequence described in reference to FIGS. 6-9.

Similar to the arrangement of latches 180 shown in FIGS. 10 and 11, as seen in FIG. 20, when lens assembly 102 is coupled to goggle frame 304, at least a portion of the latch component 186 is positioned between the outer lens 106 and latch component 184. As in FIG. 10, latch component 186 may be positioned to avoid contacting outer lens 106.

The lens assembly 102 and the goggle frame 104 may be formed of a variety of materials, for example metal, plastic (e.g., injection molded or laminated plastic materials), composite materials, or combinations thereof. The goggle frame 104 may include soft polymeric materials, such as an elastomeric material, (e.g., for comfort) typically along a portion of the goggle frame which is designed to rest against the user's forehead.

It will be further appreciated that although certain advantages or benefits are discussed with reference to some of the embodiments herein, some embodiments of the present disclosure may not provide all or any of these advantages or benefits.

All relative and directional references (including: upper, lower, upward, downward, left, right, leftward, rightward, top, bottom, side, above, below, front, middle, back, vertical, horizontal, and so forth) are given by way of example to aid the reader's understanding of the particular embodiments described herein. They should not be read to be requirements or limitations, particularly as to the position, orientation, or use unless specifically set forth in the claims. Connection references (e.g., attached, coupled, connected, joined, and the like) are to be construed broadly and may include intermediate members between a connection of elements and relative movement between elements. As such, connection references do not necessarily infer that two elements are directly connected and in fixed relation to each other, unless specifically set forth in the claims.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

What is claimed is:

1. A goggle comprising:
    a goggle frame comprising:
        a face gasket;
        an interface component coupled to the face gasket;
        a plurality of first magnetic elements coupled to one or both of the face gasket and the interface component and spaced around a periphery of the goggle frame; and
        a first latch component coupled to the interface component, wherein the first latch component comprises a lever pivotally coupled to the interface component and
    a lens assembly comprising:
        an outer lens spaced from and coupled to an inner lens by a spacer to form a dual-lens structure;
        a lens frame coupled to the inner lens, wherein the lens frame includes a number of magnet seats corresponding to a number of the plurality of first magnetic elements;
        a plurality of second magnetic elements, each positioned in a respective magnet seat on the lens frame such that the plurality of second magnetic elements is configured to magnetically couple the dual-lens assembly to the goggle frame via magnetic attraction between the first and second pluralities of magnetic elements; and a second latch component coupled to the lens frame and configured to mechanically engage the first latch component to removably secure the dual-lens assembly to the goggle frame.

2. The goggle of claim 1, wherein the interface component includes a post and the lever comprises a fulcrum portion defining an aperture configured to receive the post therein.

3. The goggle of claim 1, wherein the goggle frame further comprises an outrigger pivotally coupled to the interface component, the outrigger having a same pivotal axis as the lever.

4. The goggle of claim 3, wherein the interface component includes stops that prevent the outrigger from actuating the first latch component.

5. The goggle of claim 3, wherein the outrigger obscures at least a portion of the first latch component from view.

6. The goggle of claim 1, wherein the first latch component is coupled to the interface component such that the first latch component is biased toward a latched position.

7. The goggle of claim 6, wherein the first latch component comprises a lever including at least one arm abutting the interface component to bias the lever toward the latched position.

8. The goggle of claim 1, wherein a periphery of the spacer extends beyond a periphery of the inner lens and the lens frame is coupled to the periphery of the spacer.

9. The goggle of claim 1, wherein the face gasket comprises an upper frame ring and a lower frame ring having first and second end portions, and the interface component comprises a first side portion and a second side portion, wherein the first side portion is coupled to the upper frame ring and lower frame ring at the first end portion and the second side portion is coupled to the upper frame ring and lower frame ring at the second end portion.

10. The goggle of claim 9, further comprising first and second outriggers, the upper and lower frame rings comprising holes at the first and second end portions configured to accept prongs of the first and second outriggers to couple the first and second outriggers to the goggle frame.

11. The goggle of claim 1, wherein one of the goggle frame or the lens frame comprises a protrusion and the other one of the goggle frame and the lens frame comprises a recess configured to be received in the protrusion.

12. The goggle of claim 11, wherein the recess is located in the face gasket.

13. The goggle of claim 11, wherein the recess is located in the interface component.

14. The goggle of claim 1, wherein the lens frame further comprises at least one rim portion located around a periphery of the lens assembly such that a wearer can grasp the at least one rim portion to remove the -lens assembly from the goggle frame without touching the outer lens or inner lens.

15. The goggle of claim 14, wherein the lens assembly is semi-rimless.

16. The goggle of claim 1, Wherein the face gasket comprises upper and lower frame rings formed of thermoplastic elastomer, and wherein one or more of the plurality of first magnetic elements are coupled to at least one of the upper and lower frame rings.

17. The goggle of claim 1 wherein the interface component comprises nylon.

18. The goggle of claim 1, wherein the first plurality of magnetic elements of the goggle frame and the second plurality of magnetic elements of the lens assembly have a trapezoid shape.

19. The goggle of claim 1, wherein the lever further comprises a ledge and the second latch component comprises a tab including a shoulder, the shoulder configured to engage the ledge of the lever.

20. A goggle comprising:
a goggle frame comprising:
a face gasket;
an interface component coupled to the face gasket, the interface component comprising a post;
a plurality of first magnetic elements coupled to one or both of the face gasket and the interface component and spaced around a periphery of the goggle frame; and
a lever pivotally coupled to the post of the interface component at a fulcrum portion of the lever; the lever comprising a ledge at a first end of the lever and a user engagement portion at a second end of the lever; and
a lens assembly comprising:
a lens;
a lens frame positioned adjacent to a rear surface of the lens, wherein the lens frame includes a number of magnet seats corresponding to a number of the plurality of first magnetic elements;
a plurality of second magnetic elements, each positioned in a respective magnet seat on the lens frame such that the plurality of second magnetic elements is configured to magnetically couple the lens assembly to the goggle frame via magnetic attraction between the first and second pluralities of magnetic elements; and
a tab coupled to the lens frame, the tab including a shoulder at an end of the tab distal to the lens frame, the shoulder configured to engage the ledge of the lever to removably secure the lens assembly to the goggle frame.

21. The goggle of claim 20, wherein the lens is a first lens, and wherein the lens further comprises a second lens spaced apart from the first lens by a spacer.

22. The goggle of claim 20, frame further comprises an outrigger to which a goggle strap is coupled, wherein the outrigger conceals the tab when the lens frame is secured to the goggle frame.

23. The goggle of claim 22, wherein the outrigger is pivotally coupled to the goggle frame.

24. The goggle of claim 1, wherein the interface component includes a first side portion and a second side portion connecting an upper frame ring that provides an upper portion of the face gasket to a lower frame ring that provides a lower portion of the face gasket.

25. The goggle of claim 24, wherein the interface component is made from a more rigid material than the face gasket.

26. The goggle of claim 1, wherein the interface component includes a first side portion and a second side portion connecting an upper frame ring that provides an upper portion of the face gasket to a lower frame ring that provides a lower portion of the face gasket.

27. The goggle of claim 26, wherein the interface component is made from a more rigid material than the face gasket.

* * * * *